United States Patent
Pinto et al.

(10) Patent No.: US 10,976,318 B2
(45) Date of Patent: Apr. 13, 2021

(54) METHOD OF TREATING CANCER USING A CASPASE-4 INHIBITOR

(71) Applicant: IMMUNEPHARMA S.R.L., Fisciano (IT)

(72) Inventors: Aldo Pinto, Naples (IT); Rita Patrizia Aquino, Avellino (IT); Rosalinda Sorrentino, Sorrento (IT); Michela Terlizzi, Salerno (IT)

(73) Assignee: IMMUNEPHARMA S.R.L., Fisciano (IT)

( * ) Notice: Subject to any disclaimer, the term of this patent is extended or adjusted under 35 U.S.C. 154(b) by 0 days.

(21) Appl. No.: 15/119,544

(22) PCT Filed: Feb. 19, 2015

(86) PCT No.: PCT/IB2015/051262
§ 371 (c)(1),
(2) Date: Aug. 17, 2016

(87) PCT Pub. No.: WO2015/125098
PCT Pub. Date: Aug. 27, 2015

(65) Prior Publication Data
US 2017/0067898 A1   Mar. 9, 2017

(30) Foreign Application Priority Data

Feb. 24, 2014   (IT) .......................... RM2014A000080

(51) Int. Cl.
*G01N 33/574*   (2006.01)
*A61K 38/07*    (2006.01)
*C07K 16/40*    (2006.01)

(52) U.S. Cl.
CPC ....... *G01N 33/57423* (2013.01); *A61K 38/07* (2013.01); *C07K 16/40* (2013.01); *C07K 2317/34* (2013.01); *G01N 2333/96466* (2013.01)

(58) Field of Classification Search
CPC ... G01N 33/57423; G01N 2333/96466; A61K 38/07; C07K 16/40; C07K 2317/34; A61P 35/00
See application file for complete search history.

(56) References Cited

U.S. PATENT DOCUMENTS

2010/0009017 A1   1/2010   Cohen
2011/0165143 A1*  7/2011   Li ........................... A61K 38/06
                                                          424/94.65

FOREIGN PATENT DOCUMENTS

WO        2010/064702        6/2010
WO     WO-2010064702 A1  *   6/2010

OTHER PUBLICATIONS

National Center for Biotechnology Information (NCBI). Caspase 4, apoptosis-related cysteine peptidase [Homo sapiens]—Protein, Jul. 15, 2006.*
Mayo Clinic Patient Care and Health Info, pp. 1 and 2 (Sep. 25, 2015).*
Kim et al. "Rapid induction of apoptosis by combination of flavopiridol and tumor necrosis factor (TNF)-α or TNF-related apoptosis-inducing ligand in human cancer cell lines" *Cancer Research*, vol. 63, No. 3, pp. 621-626 (Feb. 2003).
Messerli et al. "A novel method for imaging apoptosis using a caspase-1 near-infrared fluorescent probe" *Neoplasia*, vol. 6, No. 2, pp. 95-105 (Mar. 2004).
O'Donovan et al. "Caspase 3 in breast cancer" *Clinical Cancer Research*, vol. 9, No. 2, p. 738 (Feb. 2003).
Okamoto et al. "Constitutively active inflammasome in human melanoma cells mediating autoinflammation via caspase-1 processing and secretion of interleukin-1" *Journal of Biological Chemistry*, vol. 285, No. 9, pp. 6477-6488 (Feb. 2010).
Von Schwarzenberg et al. "Targeting apoptosis pathways by natural compounds in cancer: Marine compounds as lead structures and chemical tools for cancer therapy" *Cancer Letters*, vol. 332, No. 2, pp. 295-303 (Jul. 2010).
Yamauchi et al. "Epidermal growth factor receptor tyrosine kinase defies critical prognosis genes of stage I lung adenocarcinoma" *PLOS ONE*, vol. 7, No. 9, p. e43923 (Sep. 2012).
International Search Report for PCT/IB2015/051262, eight pages (Sep. 2015).
Written Opinion of ISA for PCT/IB2015/051262, ten pages (Sep. 2015).
Dong-Myung Kim et al. "Rapid induction of apoptosis by combination of flavopiridol and tumor necrosis factor (TNF)-α or TNF-related apoptosis-inducing ligand in human cancer cell lines" *Cancer Research*, vol. 63, No. 3, pp. 621-626 (Feb. 2003).
Casson et al. "Human caspase-4 mediates noncanonical inflammasome activation against gram-negative bacterial pathogens" Proc. Natl. Acad. Sci. USA 112:6688-6693 (2015).
Grimstad et al. "TLR3 mediates release of L-1β and cell death in keratinocytes in a caspase-4 dependent manner" J. Dermatol. Sci. 72:45-53 (2013) Abstract only.
Hagar et al. "WildCARDs: Inflammatory caspases directly detect LPS" Cell Res. 25:149-150 (2015).
Huang et al. "Crosstalk between endoplasmic reticulum stress and oxidative stress in apoptosis induced by α-tocopheryl succinate in human gastric carcinoma cells" Br. J. Nutr. 109:727-735 (2013).
Kajiwara et al. "A critical role for human caspase-4 in endotoxin sensitivity" J. Immunol. 193:335-343 (2014).
Kang et al. "Caspase-4 is essential for saikosaponin α-induced apoptosis acting upstream of caspase-2 and γ-H2AX in colon cancer cells" Oncotarget 8:100433-100448 (2017).

(Continued)

*Primary Examiner* — Alana Harris Dent
(74) *Attorney, Agent, or Firm* — Sterne, Kessler, Goldstein & Fox P.L.L.C.

(57) ABSTRACT

The present invention relates to the use as a biomarker of the active form of a human caspase protein, preferably the human caspase-4 or caspase-1, or of the active form of the protein encoded by an orthologue gene of the human caspase protein, preferably by an orthologue gene of the human caspase-4, for example the murine caspase-11 protein, in a method of diagnosis and/or prognosis and/or of monitoring the progression of a tumor, particularly lung cancer.

6 Claims, 16 Drawing Sheets

Figure 1:
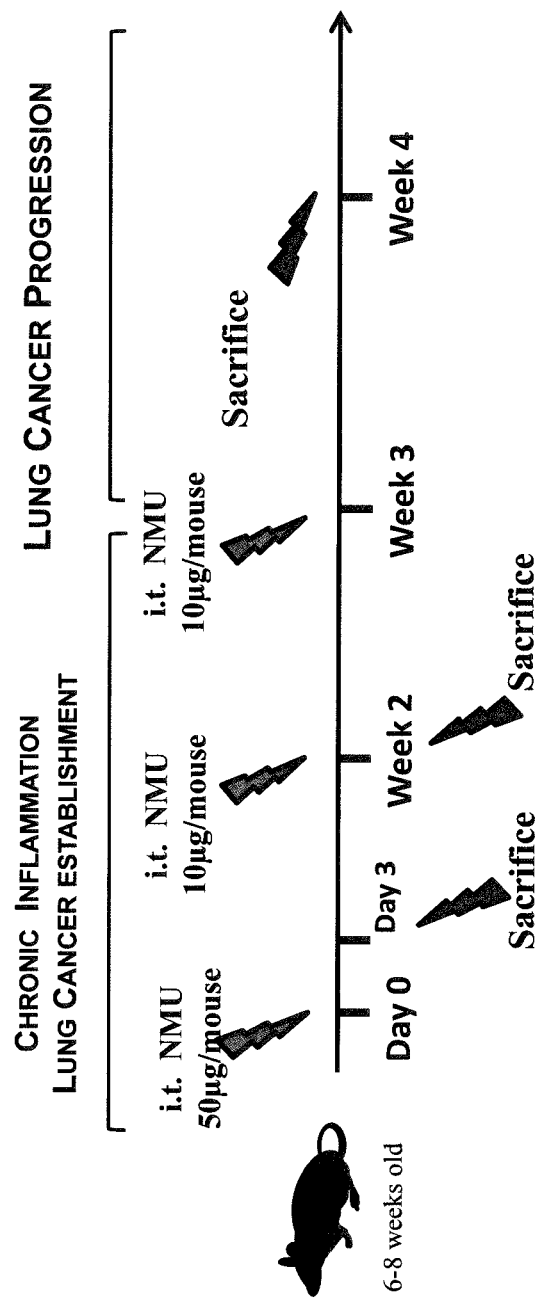

Specification includes a Sequence Listing.

(56) References Cited

OTHER PUBLICATIONS

Knodler et al. "Noncanonical inflammasome activation of caspase-4/caspase-11 mediates epithelial defenses against enteric bacterial pathogens" Cell Host Microbe 16:249-256 (2014).
Kobayashi et al. "The Shigella OspC3 effector inhibits caspase-4, antagonizes inflammatory cell death, and promotes epithelial infection" Cell Host Microbe 13:570-583 (2013).
Koyama et al. "Familial amyotrophic lateral sclerosis (FALS)-linked SOD1 mutation accelerates neuronal cell death by activating cleavage of caspase-4 under ER stress in an in vitro model of FALS" Neurochem. Int. 57:838-843 (2010).
Lakshmanan & Porter "Caspase-4 interacts with TNF receptor-associated factor 6 and mediates lipopolysaccharide-induced NF-κB-dependent production of IL-8 and CC chemokine ligand 4 (macrophage-inflammatory protein-1)" J. Immunol. 179:8480-8490 (2007).
Li et al. "Transmembrane protein 214 (TMEM214) mediates endoplasmic reticulum stress-induced caspase 4 enzyme activation and apoptosis" J. Biol. Chem. 288:17908-17917 (2013).
Li et al. "Effect of Viqi Chutan Recipe on caspase-4 and DNA-PK of cell apoptosis approach in transplanted lung cancer A549 cells in nude mice" J. Chinese Med. Mater. [Zhongyaocai] 38:1247-1250 (2015) Abstract only.
Mao et al. "Trail-induced apoptosis of human melanoma cells involves activation of caspase-4" Apoptosis 15:1211-1222 (2010) Abstract only.
Mulugeta et al. "Misfolded BRICHOS SP-C mutant proteins induce apoptosis via caspase-4-and cytochrome c-related mechanisms" Am. J. Physiol. Lung Cell Mol. Physiol. 293:L720-729 (2007).
Sollberger et al. "Caspase-4 is required for activation of inflammasomes" J. Immunol. 188:1992-2000 (2012).
Valentin-Acevedo et al. "c-Rel deficiency increases caspase-4 expression and leads to ER stress and necrosis in EBV-transformed cells" PLoS ONE 6:e25467 (2011).
Vigano et al. "Human caspase-4 and caspase-5 regulate the one-step non-canonical inflammasome activation in monocyte" Nature Comm. 6:8761 (2015).
Xie et al. "HL-37, a novel anthracene derivative, induces $Ca^{2+}$-mediated apoptosis in human breast cancer cells" Toxicology 254:68-74 (2008) Abstract only.
Yamamuro et al. "Caspase-4 directly activates caspase-9 in endoplasmic reticulum stress-induced apoptosis in SH-SYSY cells" J. Pharmacol. Sci. 115:239-243 (2011).
Yang et al. "Non-canonical activation of inflammatory caspases by cytosolic LPS in innate immunity" Curr. Opin. Immunol. 32:78-83 (2015).
Yang et al. "NF-κB regulates caspase-4 expression and sensitizes neuroblastoma cells to Fas-induced apoptosis" PLoS ONE 10:e0117953 (2015).
Yang et al. "Direct cytotoxicity produced by adenoviral-mediated interferon a gene transfer in interferon-resistant cancer cells involves ER stress and caspase 4 activation" Cancer Gene Ther. 18:609-616 (2011).

\* cited by examiner

Fig. 2A    Fig. 2B    Fig. 2C
NMU-induced lung tumor
4 wks 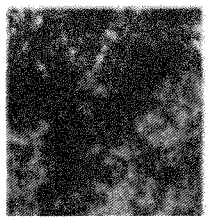 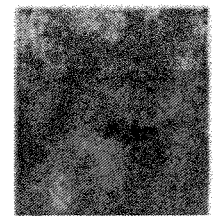 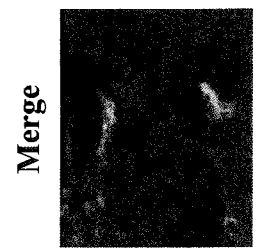 Merge
7 days 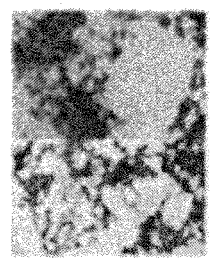 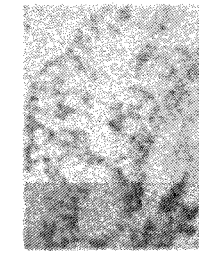 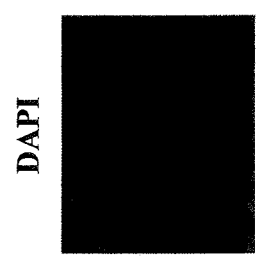 DAPI
Vehicle 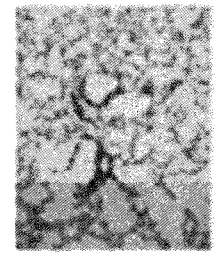 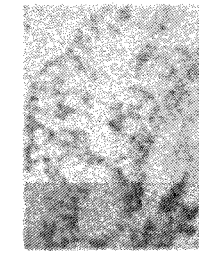 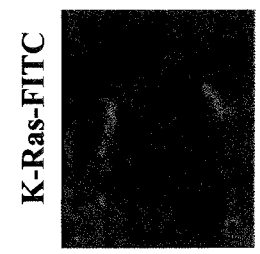 K-Ras-FITC
H&E    Ki-67    K-Ras

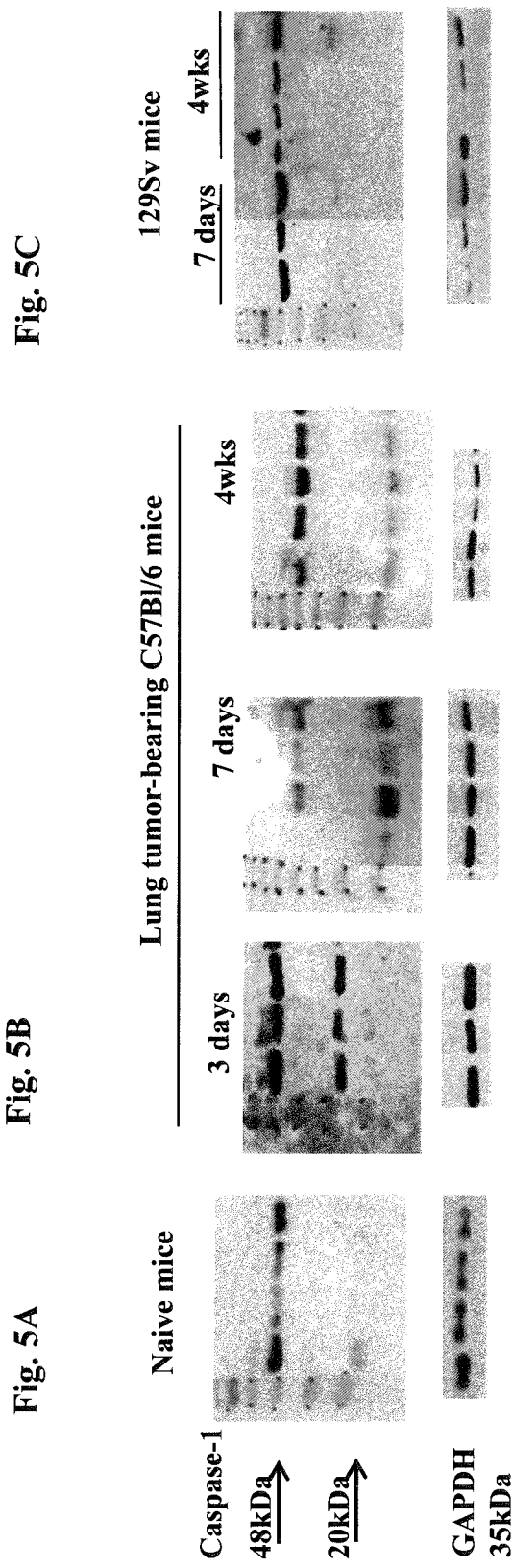

IP = immunoprecipitation
WB = western blotting

SEQUENCE LISTING

```
<160> NUMBER OF SEQ ID NOS: 29

<210> SEQ ID NO 1
<211> LENGTH: 377
<212> TYPE: PRT
<213> ORGANISM: Homo sapiens

<400> SEQUENCE: 1

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
    210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
```

```
            305                 310                 315                 320
        Ile Phe Ile Thr Gln Leu Ile Thr Cys Phe Gln Lys Tyr Ser Trp Cys
                        325                 330                 335

Cys His Leu Glu Glu Val Phe Arg Lys Val Gln Gln Ser Phe Glu Thr
                        340                 345                 350

Pro Arg Ala Lys Ala Gln Met Pro Thr Ile Glu Arg Leu Ser Met Thr
                        355                 360                 365

Arg Tyr Phe Tyr Leu Phe Pro Gly Asn
                        370                 375

<210> SEQ ID NO 2
<211> LENGTH: 404
<212> TYPE: PRT
<213> ORGANISM: Homo sapiens

<400> SEQUENCE: 2

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
        50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
    290                 295                 300
```

```
Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
            325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
        370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 3
<211> LENGTH: 402
<212> TYPE: PRT
<213> ORGANISM: Mus musculus

<400> SEQUENCE: 3

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
    50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly His Pro Ser Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
    210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
                245                 250                 255

Val Asp Thr Ile Phe Gln Met Met Asn Thr Leu Lys Cys Pro Ser Leu
            260                 265                 270
```

```
Lys Asp Lys Pro Lys Val Ile Ile Gln Ala Cys Arg Gly Glu Lys
            275                 280                 285

Gln Gly Val Val Leu Leu Lys Asp Ser Val Arg Asp Ser Glu Asp
290                 295                 300

Phe Leu Thr Asp Ala Ile Phe Glu Asp Gly Ile Lys Lys Ala His
305                 310                 315                 320

Ile Glu Lys Asp Phe Ile Ala Phe Cys Ser Thr Pro Asp Asn Val
                325                 330                 335

Ser Trp Arg His Pro Val Arg Gly Ser Leu Phe Ile Glu Ser Leu Ile
            340                 345                 350

Lys His Met Lys Glu Tyr Ala Trp Ser Cys Asp Leu Gly Asp Ile Phe
            355                 360                 365

Arg Lys Val Arg Phe Ser Phe Glu Gln Pro Glu Phe Arg Leu Gln Met
370                 375                 380

Pro Thr Ala Asp Arg Val Thr Leu Thr Lys Arg Phe Tyr Leu Phe Pro
385                 390                 395                 400

Gly His

<210> SEQ ID NO 4
<211> LENGTH: 373
<212> TYPE: PRT
<213> ORGANISM: Mus musculus

<400> SEQUENCE: 4

Met Ala Glu Asn Lys His Pro Asp Lys Pro Leu Lys Val Leu Glu Gln
1               5                   10                  15

Leu Gly Lys Glu Val Leu Thr Glu Tyr Leu Glu Lys Leu Val Gln Ser
            20                  25                  30

Asn Val Leu Lys Leu Lys Glu Glu Asp Lys Gln Lys Phe Asn Asn Ala
        35                  40                  45

Glu Arg Ser Asp Lys Arg Trp Val Phe Val Asp Ala Met Lys Lys Lys
50                  55                  60

His Ser Lys Val Gly Glu Met Leu Leu Gln Thr Phe Phe Ser Val Asp
65                  70                  75                  80

Pro Gly Ser His His Gly Glu Ala Asn Leu Glu Met Glu Glu Pro Glu
                85                  90                  95

Glu Ser Leu Asn Thr Leu Lys Leu Cys Ser Pro Glu Glu Phe Thr Arg
            100                 105                 110

Leu Cys Arg Glu Lys Thr Gln Glu Ile Tyr Pro Ile Lys Glu Ala Asn
        115                 120                 125

Gly Arg Thr Arg Lys Ala Leu Ile Ile Cys Asn Thr Glu Phe Lys His
130                 135                 140

Leu Ser Leu Arg Tyr Gly Ala Asn Phe Asp Ile Ile Gly Met Lys Gly
145                 150                 155                 160

Leu Leu Glu Asp Leu Gly Tyr Asp Val Val Val Lys Glu Glu Leu Thr
                165                 170                 175

Ala Glu Gly Met Glu Ser Glu Met Lys Asp Phe Ala Ala Leu Ser Glu
            180                 185                 190

His Gln Thr Ser Asp Ser Thr Phe Leu Val Leu Met Ser His Gly Thr
        195                 200                 205

Leu His Gly Ile Cys Gly Thr Met His Ser Glu Lys Thr Pro Asp Val
210                 215                 220

Leu Gln Tyr Asp Thr Ile Tyr Gln Ile Phe Asn Asn Cys His Cys Pro
225                 230                 235                 240
```

Gly Leu Arg Asp Lys Pro Lys Val Ile Ile Val Gln Ala Cys Arg Gly
                245                 250                 255

Gly Asn Ser Gly Glu Met Trp Ile Arg Glu Ser Ser Lys Pro Gln Leu
            260                 265                 270

Cys Arg Gly Val Asp Leu Pro Arg Asn Met Glu Ala Asp Ala Val Lys
        275                 280                 285

Leu Ser His Val Glu Lys Asp Phe Ile Ala Phe Tyr Ser Thr Thr Pro
    290                 295                 300

His His Leu Ser Tyr Arg Asp Lys Thr Gly Ser Tyr Phe Ile Thr
305                 310                 315                 320

Arg Leu Ile Ser Cys Phe Arg Lys His Ala Cys Ser Cys His Leu Phe
                325                 330                 335

Asp Ile Phe Leu Lys Val Gln Gln Ser Phe Glu Lys Ala Ser Ile His
            340                 345                 350

Ser Gln Met Pro Thr Ile Asp Arg Ala Thr Leu Thr Arg Tyr Phe Tyr
        355                 360                 365

Leu Phe Pro Gly Asn
    370

<210> SEQ ID NO 5
<211> LENGTH: 354
<212> TYPE: PRT
<213> ORGANISM: Mus musculus

<400> SEQUENCE: 5

Met Glu Ser Glu Tyr Arg Glu Met Leu Leu Leu Thr Gly Leu Asp His
1               5                   10                  15

Ile Thr Glu Glu Glu Leu Lys Arg Phe Lys Tyr Phe Ala Leu Thr Glu
            20                  25                  30

Phe Gln Ile Ala Arg Ser Thr Leu Asp Val Ala Asp Arg Thr Glu Leu
        35                  40                  45

Ala Asp His Leu Ile Gln Ser Ala Gly Ala Ala Ser Ala Val Thr Lys
    50                  55                  60

Ala Ile Asn Ile Phe Gln Lys Leu Asn Tyr Met His Ile Ala Asn Ala
65                  70                  75                  80

Leu Glu Glu Lys Lys Lys Glu Ala Glu Arg Lys Leu Met Thr Asn Thr
                85                  90                  95

Lys Lys Arg Gly Thr Gln Lys Val Glu Asn Arg Ser Gln Ala Glu Asn
            100                 105                 110

Cys Ser Ala Ala Ser Ala Thr Arg Ser Asp Asn Asp Phe Lys Glu Gln
        115                 120                 125

Ala Ala Thr Glu Val Cys Pro Gln Ala Lys Pro Gln Lys Lys Gln Met
    130                 135                 140

Val Ala Glu Gln Glu Ala Ile Arg Glu Asp Leu Gln Lys Asp Pro Leu
145                 150                 155                 160

Val Val Thr Val Leu Lys Ala Ile Asn Pro Phe Glu Cys Glu Thr Gln
                165                 170                 175

Glu Gly Arg Gln Glu Ile Phe His Ala Thr Val Ala Thr Glu Thr Asp
            180                 185                 190

Phe Phe Phe Val Lys Val Leu Asn Ala Gln Phe Lys Asp Lys Phe Ile
        195                 200                 205

Pro Lys Arg Thr Ile Lys Ile Ser Asn Tyr Leu Trp His Ser Asn Phe
    210                 215                 220

Met Glu Val Thr Ser Ser Ser Val Val Val Asp Val Glu Ser Asn His
225                 230                 235                 240

```
Glu Val Pro Asn Asn Val Val Lys Arg Ala Arg Thr Pro Arg Ile
                245                 250                 255

Ser Lys Leu Lys Ile Gln Pro Cys Gly Thr Ile Val Asn Gly Leu Phe
            260                 265                 270

Lys Val Gln Lys Ile Thr Glu Glu Lys Asp Arg Val Leu Tyr Gly Ile
            275                 280                 285

His Asp Lys Thr Gly Thr Met Glu Val Leu Val Leu Gly Asn Pro Ser
            290                 295                 300

Lys Thr Lys Cys Glu Glu Gly Asp Lys Ile Arg Leu Thr Phe Phe Glu
305                 310                 315                 320

Val Ser Lys Asn Gly Val Lys Ile Gln Leu Lys Ser Gly Pro Cys Ser
                325                 330                 335

Phe Phe Lys Val Ile Lys Ala Ala Lys Pro Lys Thr Asp Met Lys Ser
            340                 345                 350

Val Glu

<210> SEQ ID NO 6
<211> LENGTH: 343
<212> TYPE: PRT
<213> ORGANISM: Homo sapiens

<400> SEQUENCE: 6

Met Glu Ser Lys Tyr Lys Glu Ile Leu Leu Leu Thr Gly Leu Asp Asn
1               5                   10                  15

Ile Thr Asp Glu Glu Leu Asp Arg Phe Lys Phe Phe Leu Ser Asp Glu
                20                  25                  30

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
        50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys Gln Tyr Lys Ser Val Thr
                85                  90                  95

Lys Pro Lys Pro Leu Ser Gln Ala Glu Met Ser Pro Ala Ala Ser Ala
            100                 105                 110

Ala Ile Arg Asn Asp Val Ala Lys Gln Arg Ala Ala Pro Lys Val Ser
            115                 120                 125

Pro His Val Lys Pro Glu Gln Lys Gln Met Val Ala Gln Gln Glu Ser
            130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                165                 170                 175

Phe His Ala Thr Val Ala Thr Glu Lys Glu Phe Phe Phe Val Lys Val
            180                 185                 190

Phe Asn Thr Leu Leu Lys Asp Lys Phe Ile Pro Lys Arg Ile Ile Ile
            195                 200                 205

Ile Ala Arg Tyr Tyr Arg His Ser Gly Phe Leu Glu Val Asn Ser Ala
        210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                245                 250                 255
```

```
Thr Gln Pro Leu Gly Thr Ile Val Asn Gly Leu Phe Val Val Gln Lys
            260                 265                 270

Val Thr Glu Lys Lys Asn Ile Leu Phe Asp Leu Ser Asp Asn Thr
        275                 280                 285

Gly Lys Met Glu Val Leu Gly Val Arg Asn Glu Asp Thr Met Lys Cys
290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
            325                 330                 335

Ile Lys Ala Lys Lys Lys Thr
            340
```

<210> SEQ ID NO 7
<211> LENGTH: 269
<212> TYPE: PRT
<213> ORGANISM: Mus musculus

<400> SEQUENCE: 7

```
Ala Lys Val Pro Asp Leu Phe Glu Asp Leu Lys Asn Cys Tyr Ser Glu
1               5                   10                  15

Asn Glu Asp Tyr Ser Ser Ala Ile Asp His Leu Ser Leu Asn Gln Lys
            20                  25                  30

Ser Phe Tyr Asp Ala Ser Tyr Gly Ser Leu His Glu Thr Cys Thr Asp
        35                  40                  45

Gln Phe Val Ser Leu Arg Thr Ser Glu Thr Ser Lys Met Ser Asn Phe
    50                  55                  60

Thr Phe Lys Glu Ser Arg Val Thr Val Ser Ala Thr Ser Ser Asn Gly
65                  70                  75                  80

Lys Ile Leu Lys Lys Arg Arg Leu Ser Phe Ser Glu Thr Phe Thr Glu
            85                  90                  95

Asp Asp Leu Gln Ser Ile Thr His Asp Leu Glu Glu Thr Ile Gln Pro
        100                 105                 110

Arg Ser Ala Pro Tyr Thr Tyr Gln Ser Asp Leu Arg Tyr Lys Leu Met
    115                 120                 125

Lys Leu Val Arg Gln Lys Phe Val Met Asn Asp Ser Leu Asn Gln Thr
130                 135                 140

Ile Tyr Gln Asp Val Asp Lys His Tyr Leu Ser Thr Thr Trp Leu Asn
145                 150                 155                 160

Asp Leu Gln Gln Glu Val Lys Phe Asp Met Tyr Ala Tyr Ser Ser Gly
            165                 170                 175

Gly Asp Asp Ser Lys Tyr Pro Val Thr Leu Lys Ile Ser Asp Ser Gln
        180                 185                 190

Leu Phe Val Ser Ala Gln Gly Glu Asp Gln Pro Val Leu Leu Lys Glu
    195                 200                 205

Leu Pro Glu Thr Pro Lys Leu Ile Thr Gly Ser Glu Thr Asp Leu Ile
210                 215                 220

Phe Phe Trp Lys Ser Ile Asn Ser Lys Asn Tyr Phe Thr Ser Ala Ala
225                 230                 235                 240

Tyr Pro Glu Leu Phe Ile Ala Thr Lys Glu Gln Ser Arg Val His Leu
            245                 250                 255

Ala Arg Gly Leu Pro Ser Met Thr Asp Phe Gln Ile Ser
        260                 265
```

-continued

<210> SEQ ID NO 8
<211> LENGTH: 271
<212> TYPE: PRT
<213> ORGANISM: Homo sapiens

<400> SEQUENCE: 8

Met Ala Lys Val Pro Asp Met Phe Glu Asp Leu Lys Asn Cys Tyr Ser
1               5                   10                  15

Glu Asn Glu Glu Asp Ser Ser Ile Asp His Leu Ser Leu Asn Gln
            20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
        50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
130                 135                 140

Ile Arg Ala Asn Asp Gln Tyr Leu Thr Ala Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 9
<211> LENGTH: 269
<212> TYPE: PRT
<213> ORGANISM: Mus musculus

<400> SEQUENCE: 9

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
            20                  25                  30

Gly Cys Phe Gln Thr Phe Asp Leu Gly Cys Pro Asp Glu Ser Ile Gln
            35                  40                  45

Leu Gln Ile Ser Gln Gln His Ile Asn Lys Ser Phe Arg Gln Ala Val
        50                  55                  60

Ser Leu Ile Val Ala Val Glu Lys Leu Trp Gln Leu Pro Val Ser Phe

```
            65                  70                  75                  80
Pro Trp Thr Phe Gln Asp Glu Asp Met Ser Thr Phe Ser Phe Ile
                    85                  90                  95

Phe Glu Glu Glu Pro Ile Leu Cys Asp Ser Trp Asp Asp Asp Asn
                100                 105                 110

Leu Leu Val Cys Asp Val Pro Ile Arg Gln Leu His Tyr Arg Leu Arg
            115                 120                 125

Asp Glu Gln Gln Lys Ser Leu Val Leu Ser Asp Pro Tyr Glu Leu Lys
        130                 135                 140

Ala Leu His Leu Asn Gly Gln Asn Ile Asn Gln Gln Val Ile Phe Ser
145                 150                 155                 160

Met Ser Phe Val Gln Gly Glu Pro Ser Asn Asp Lys Ile Pro Val Ala
                165                 170                 175

Leu Gly Leu Lys Gly Lys Asn Leu Tyr Leu Ser Cys Val Met Lys Asp
            180                 185                 190

Gly Thr Pro Thr Leu Gln Leu Glu Ser Val Asp Pro Lys Gln Tyr Pro
        195                 200                 205

Lys Lys Lys Met Glu Lys Arg Phe Val Phe Asn Lys Ile Glu Val Lys
    210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
                260                 265

<210> SEQ ID NO 10
<211> LENGTH: 269
<212> TYPE: PRT
<213> ORGANISM: Homo sapiens

<400> SEQUENCE: 10

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175
```

-continued

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
            245                 250                 255

Gln Asp Ile Thr Asp Phe Thr Met Gln Phe Val Ser Ser
            260                 265

<210> SEQ ID NO 11
<211> LENGTH: 215
<212> TYPE: PRT
<213> ORGANISM: Mus musculus

<400> SEQUENCE: 11

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu Glu
            180                 185                 190

Asp Glu Glu Asp Glu Glu Glu Glu Glu Glu Asp Glu Asp Glu Glu Glu
        195                 200                 205

Glu Glu Asp Asp Asp Asp Glu
    210                 215

<210> SEQ ID NO 12
<211> LENGTH: 215
<212> TYPE: PRT
<213> ORGANISM: Homo sapiens

<400> SEQUENCE: 12

Met Gly Lys Gly Asp Pro Lys Lys Pro Arg Gly Lys Met Ser Ser Tyr
1               5                   10                  15

```
Ala Phe Phe Val Gln Thr Cys Arg Glu His Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Asp Glu Glu Asp Glu Asp Glu
            195                 200                 205

Glu Glu Asp Asp Asp Asp Asp
210                 215

<210> SEQ ID NO 13
<211> LENGTH: 192
<212> TYPE: PRT
<213> ORGANISM: Mus musculus

<400> SEQUENCE: 13

Met Ala Ala Met Ser Glu Asp Ser Cys Val Asn Phe Lys Glu Met Met
1               5                   10                  15

Phe Ile Asp Asn Thr Leu Tyr Phe Ile Pro Glu Glu Asn Gly Asp Leu
            20                  25                  30

Glu Ser Asp Asn Phe Gly Arg Leu His Cys Thr Thr Ala Val Ile Arg
            35                  40                  45

Asn Ile Asn Asp Gln Val Leu Phe Val Asp Lys Arg Gln Pro Val Phe
50                  55                  60

Glu Asp Met Thr Asp Ile Asp Gln Ser Ala Ser Glu Pro Gln Thr Arg
65                  70                  75                  80

Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
            115                 120                 125

Ile Gln Ser Asp Leu Ile Phe Phe Gln Lys Arg Val Pro Gly His Asn
130                 135                 140

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175
```

```
Asn Gly Asp Lys Ser Val Met Phe Thr Leu Thr Asn Leu His Gln Ser
            180                 185                 190
```

<210> SEQ ID NO 14
<211> LENGTH: 193
<212> TYPE: PRT
<213> ORGANISM: Homo sapiens

<400> SEQUENCE: 14

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 15
<211> LENGTH: 50
<212> TYPE: PRT
<213> ORGANISM: Homo sapiens
<220> FEATURE:
<223> OTHER INFORMATION: Synthetic peptide

<400> SEQUENCE: 15

```
Gly Ile Leu Glu Gly Ile Cys Gly Thr Val His Asp Glu Lys Lys Pro
1               5                   10                  15

Asp Val Leu Leu Tyr Asp Thr Ile Phe Gln Ile Phe Asn Asn Arg Asn
            20                  25                  30

Cys Leu Ser Leu Lys Asp Lys Pro Lys Val Ile Val Gln Ala Cys
            35                  40                  45

Arg Gly
    50
```

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

```
<400> SEQUENCE: 16

Ser Pro Asn Lys Lys Ala His Pro Asn Met Glu Ala Gly Pro Cys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Lys Lys Lys Tyr Tyr Asp Ala Lys Thr Glu Asp Lys Val Arg Cys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Cys Ala Ser Ser Gln Ser Ser Glu Asn Leu Glu Glu Asp Ala Val
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Met Ala Glu Gly Asn His Arg Lys Lys Pro Leu Lys Val Leu Cys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Cys Gln Ser Phe Glu Thr Pro Arg Ala Lys Ala Gln Met Pro Thr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Pro Glu Ser Gly Glu Ser Thr Asp Ala Leu Lys Leu Cys Pro Cys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 22

Cys Thr Glu Phe Asp His Leu Pro Pro Arg Asn Gly Ala Asp Phe
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Cys Gly Leu Asp Tyr Ser Val Asp Val Glu Glu Asn Leu Thr Ala
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide

<400> SEQUENCE: 24

Cys Gly Thr Val His Asp Glu Lys Lys Pro Asp Val Leu Leu
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Cys Gly Ala Asn Arg Gly Glu Leu Trp Val Arg Asp Ser Pro Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Cys Ser Ala Leu Arg Ala Phe Ala Thr Arg Pro Glu His Lys Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Cys Ile Tyr Pro Ile Lys Glu Arg Asn Asn Arg Thr Arg Leu Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28
```

```
Cys Ile Phe Asn Asn Arg Asn Cys Leu Ser Leu Lys Asp Lys Pro
1               5                   10                  15
```

<210> SEQ ID NO 29
<211> LENGTH: 1319
<212> TYPE: RNA
<213> ORGANISM: Homo sapiens
<220> FEATURE:
<221> NAME/KEY: source
<222> LOCATION: 1..1319
<223> OTHER INFORMATION: /mol_type="mRNA"
      /organism="Homo sapiens"

<400> SEQUENCE: 29

```
auacauaguu uacuuucauu uuugacucug aggcucuuuc caacgcugua aaaaaggaca    60
gaggcuguuc ccuauggcag aaggcaacca cagaaaaaag ccacuuaagg uguuggaauc   120
ccugggcaaa gauuuccuca cugguguuuu ggauaacuug guggaacaaa auguacugaa   180
cuggaaggaa gaggaaaaaa agaaauauua cgaugcuaaa acugaagaca aaguucgggu   240
caugggcagac ucuaugcaag agaagcaacg uauggcagga caaaugcuuc uucaaaccuu   300
uuuuaacaua gaccaaauau cccccaauaa aaaagcucau ccgaauaugg aggcuggacc   360
accugaguca ggagaaucua cagaugcccu caagcuuugu ccucaugaag aauuccugag   420
acuauguaaa gaaagagcug aagagaucua uccaauaaag gagagaaaca accgcacacg   480
ccuggcucuc aucauaugca auacagaguu ugaccaucug ccuccgagga auggagcuga   540
cuuugacauc acagggauga aggagcuacu ugagggucug gacuauagug uagauguaga   600
agagaaucug acagccaggg auauggaguc agcgcugagg gcauuugcua ccagaccaga   660
gcacaagucc ucugacagca cauucuuggu acucaugucu cauggcaucc uggagggaau   720
cugcggaacu gugcaugaug agaaaaaacc agaugugcug cuuuaugaca ccaucuucca   780
gauauucaac aaccgcaacu gccucagucu gaaggacaaa cccaaggcua ucauugccca   840
ggccugcaga ggugcaaacc guggggaacu guggggucaga gacucuccag cauccuugga   900
aguggccucu ucacagucau cugagaaccu agaggaagau gcuguuuaca agacccacgu   960
ggagaaggac uucauugcuu ucugcucuuc aacgccacac aacguguccu ggagagacag  1020
cacaaugggc ucuaucuuca ucacacaacu caucacaugc uuccagaaau auucuuggug  1080
cugccaccua gaggaaguau uucggaaggu acagcaauca uuugaaacuc caagggccaa  1140
agcucaaaug cccaccauag aacgacuguc caugacaaga uauuucuacc ucuuuccugg  1200
caauugaaaa uggaagccac aagcagccca gcccuccuua aucaacuuca aggagcaccu  1260
ucauuaguac agcuugcaua uuuaacauuu uguauuucaa uaaaagugaa gacaaacga   1319
```

METHOD OF TREATING CANCER USING A CASPASE-4 INHIBITOR

This application is the U.S. national phase of International Application No. PCT/IB2015/051262 filed 19 Feb. 2015, which designated the U.S. and claims priority to Italian Application No. RM2014A000080, filed 24 Feb. 2014; the entire contents of each of which are hereby incorporated by reference.

The present invention relates to the use as a biomarker of the active form of a human caspase protein, preferably the human caspase-4 or caspase-1, or of the active form of the protein encoded by an orthologue gene of the human caspase protein, preferably by an orthologue gene of the human caspase-4, for example the murine caspase-11 protein, in a method of diagnosis and/or prognosis and/or of monitoring the progression of a tumor, particularly lung cancer.

PRIOR ART

Lung cancer is one of the leading causes of death in industrialized countries, characterized by a poor prognosis and a low survival rate (Jett et al., 1983; Pinto et al., 2011). One of the risk factors for lung cancer is the exposure (inhalation) to carcinogens (Valavanidis et al., 2008), although the cellular and molecular mechanisms underlying the neoplastic growth is not well defined yet.

The strict correlation between the onset/development of neoplastic diseases and the immune system (Coussens et al., 2013; Pinto et al., 2011; Zitvogel et al., 2012) is of recent scientific interest. Chronic inflammation is a common denominator of many respiratory diseases, including lung cancer. It is well known that neoplasm development/progression is associated with an immunosuppressive environment that facilitates the growth of tumor cells beyond the anti-neoplastic immune control (Coussens et al., 2013). In spite of classic chemotherapy, a concept that currently seems to play an increasingly important role in the treatment of neoplasms is the involvement, and especially the 'pharmacological manipulation', of the immune system in the tumor microenvironment.

To date, the most widely currently used immunotherapy consists of leukocytes activation in order to obtain an antitumor immune response (Coussens et al., 2013). Nevertheless, the recognition of the specific molecular and cellular mechanisms involved in chronic inflammation underlying the neoplastic growth, appears to be of greatest scientific impact in the identification of pharmacological targets that can modulate the neoplastic growth.

Lung epithelial cells, macrophages (MΦ) and tissue dendritic cells (DCs) are the first line of defence from external attacks, and they are responsible for the ensuing adaptive immune response (Pinto et al., 2011). Continuous insult/s to these cells promote and support a chronic inflammatory response characterized by the release of molecules called alarmins (Paul-Clark et al., 2012), including IL-1α, IL-1β, high mobility group box 1 (HMGB1). The synthesis/release of such alarmins is finely regulated by a multi-protein system called inflammasome according to a caspase-1 dependent canonical pathway (Latz et al., 2013), and a caspase-11-dependent non-canonical pathway (Kayagaki et al., 2013). Caspase-1 activation converts pro-IL-1β and pro-IL-18 into their active forms (Lamkanfi and Dixit, 2012). Conversely, caspase-11 promotes the release of IL-1α and HMGB1 (Ng and Monack, 2013). Both caspase-1 and -11 are capable of inducing pyropoptosis, cell death which differs from apoptosis as it induces a pro-inflammatory response, (Lamkanfi and Dixit, 2012) that in a tumor context could facilitate an immunosuppression state that favours the neoplastic growth.

The inflammasome complex is orchestrated by the activity of cytosolic proteins called Nod-like Receptors (NLRs), and more generally pathogen recognition receptors (PRRs), able to recognize exogenous (pathogen-associated molecular patterns: PAMPs) and endogenous (Danger-associated molecular patterns: DAMPs) ligands that act upstream of caspase-1-dependent pathway (Caffrey and Fitzgerald, 2012). To date, twenty-two NLRs have been identified. Though, the intracytoplasmic NLRP3 receptor is certainly the most studied so far, and its role in cancer seems to be still controversial (Zitvogel et al., 2012). In fact, NLRP3 plays a protective role in colon carcinoma, as its genetic absence facilitates tumor growth associated with a higher chronic inflammation in the colon epithelium (Allen et al., 2010). Moreover, NLRP3 seems to be essential for the activity of certain classic chemotherapy agents, such as doxorubicin and 5-fluorouracil (Ghiringhelli et al., 2009). In sharp contrast, in a murine model of lung metastasis and fibrosarcoma, NLRP3 activation promotes tumor growth (Chow et al., 2012a), facilitating the recruitment of cells having immunosuppressive activity, such as the myeloid-derived suppressor cells (MDSC) that not only inhibit the cytotoxic T lymphocytes activity (cytotoxic T lymphocytes: CTLs), but also the natural killer cells (NK). In addition, although not essential for the neoplastic growth (Chow et al., 2012b), NLRP3 seems to be involved in lung inflammation induced by asbestos and silica, promoters of mesothelioma (Dostert et al., 2008). Caspase-11, a murine analogue of human caspase-4, is a key enzyme for the activation of the non-canonical inflammasome pathway (Ng and Monack, 2013). As a result of pro-inflammatory conditions and especially of cell necrosis by pathogenic infections, this enzyme is able to induce proteolysis of the mature form of IL-1α, and the release of HMGB1 in the extracellular matrix (Ng and Monack, 2013). To date, it is described in the literature that, during bacterial infections, caspase-11 is activated in a type I interferon-dependent way through the TIR-domain-containing adapter-inducing interferon-β (TRIF) transduction pathway, which underlies the activation of some Toll Like Receptor (TLR), such as TLR4 and TLR3 (Bortoluci and Medzhitov, 2010). Both the role of the murine caspase-11 and of the analogue human caspase-4 in cancer, particularly in lung cancer, is still completely unknown. Therefore, in light of an increasingly emerging literature, several aspects of the inflammasome biology are still unexplored, especially in the field of lung oncology, in which chronic inflammation appears to be a promoter of the neoplastic growth (Coussens et al., 2013).

The patent application WO2008/009028 relates to a method for determining the prognosis of a subject with lung adenocarcinoma, comprising the quantification of the expression of several cytokines, some of which are not correlated to the murine caspase 11 or the human caspase 4.

Furthermore, in M. Yamauchi et al., (2010) the identification of 139 gefitinib-sensitive genes, including also the caspase 4 gene, in human primary lung tumor epithelial cells, by analysis of the gene expression profile, is described.

In the patent application WO2010/064702, a method for the diagnosis of lung cancer by analysis of the variation of the genetic expression of 227 genes, including the genes for caspase-1 and caspase-4, is described. However, the use of an active form of the human caspase protein as a biomarker involved in lung cancer was never described or suggested before. Moreover, the link between the pro-inflammatory cytokine effectors of the murine caspase-11 or human caspase-4, such as IL-1α, and lung cancer was neither known nor suggested.

DESCRIPTION OF THE INVENTION

The authors have surprisingly found that the caspases, especially the murine caspase-11 [NCBI accession number CAA73531.1] (SEQ ID No. 4) and the human analogue caspase-4 [NCBI accession number NP_001216.1] (SEQ ID No. 1), and the murine caspase-1 [NCBI accession number mouse: NP_033937.2 (NM_009807.2)] (SEQ ID No. 3) and human caspase-1 [CAA46153.1] (SEQ ID No. 2) are involved in neoplastic growth in the lung.

Moreover, although the molecular ligands which are activators of these enzymes are not known yet, the present authors identified a new "activation signalling pathway", involved in lung tumor growth, which is useful to identify new therapeutic and diagnostic targets. During oxidative stress induced by exposure to carcinogens, there is the production of 8-hydroxy-2'-deoxyguanosine (8-OH-dG), which is in turn recognized by the intracytoplasmic receptor AIM2 [NCBI accession numbers: mouse: NP_001013801.2] (SEQ ID No. 5), human [NP_004824.1] (SEQ ID No. 6), a component of the inflammasome complex.

AIM2 binds to caspase-11, in the mouse, and to caspase-4, in humans, which active form induces the release of alarmins such as IL-1α [NCBI 10 accession numbers: mouse: NP_034684 [GI: 47059075]] (SEQ ID No. 7); and human [NP_000566 [GI: 27894330] ] (SEQ ID No. 8:), and IL-1β [NCBI accession number mouse: NP_032387.1 [GI: 6680415]] (SEQ ID No. 9) and human: NP_000567.1 [GI: 10835145]] (SEQ ID No. 10) and HMGB1 [NCBI accession numbers: mouse AAI10668 [GI 84040262]] (SEQ ID No. 11); human: CAG 33144.1 [GI 48145843] (SEQ ID No. 12), facilitating lung tumorigenesis. Moreover, in human lung carcinoma tissues, the binding of AIM2 to caspase-4 is very pronounced. A further confirmation of what we state is the observation that, in mice without functional caspase-11 (129Sv mice) or caspase-1/11 knockout mice, or following neutralization of caspase-11 by means of a specific monoclonal against caspase-11 or IL-1α, an effector of caspase-11, a significant reduction in the development of lung tumor growth is observed, compared to mice with an intact and active caspase-11 (C57Bl/6 mice).

The link between the activation of caspase-1 (p20 kDa) and lung cancer was also identified by these authors.

Therefore, the authors not only identified a new "pathway" involved in lung carcinogenesis, but also identified new pharmacological targets for the development of future therapeutic strategies for a disease with high mortality, such as lung carcinoma. Furthermore, the activation of caspase-4 in humans, associated with the presence of pro-inflammatory cytokines, such as IL-1α and IL-1β, already known to be at very high levels in tumor tissues, represent a new diagnostic, and possibly prognostic, tool for lung cancer.

It is therefore an embodiment of the invention a biomarker belonging to the group consisting of at least:
  a) the active form of a human caspase protein;
  b) a variant, homologue, a derivative or functional fragment thereof;
  c) the active form of the protein encoded by an orthologue gene of said human caspase protein gene,
  for use in a method for diagnosis and/or prognosis and/or for monitoring of the progression of a tumor.

Said human caspase protein is preferably the human caspase-4 protein (SEQ ID No. 1) or the human caspase-1 protein (SEQ ID No. 2). An orthologue gene of the human caspase-4 gene is, for example, the murine caspase-11 gene.

Said tumor is preferably lung tumor, more preferably lung carcinoma.

A further embodiment of the invention is an in vitro method for diagnosis and/or prognosis and/or for monitoring of the progression of a tumor comprising the steps of:
  a) detection and/or quantification of the biomarker as defined above in a sample isolated from a subject, and
  b) comparison with an adequate control.

The quantification of the biomarker may correspond to the measurement of the amount, or to the measurement of an alteration in the amount, of the biomarker, more particularly to an increase or a decrease in the amount of the biomarker. An increase may be related to a worsening of the tumor. A decrease may be related to an improvement of the tumor, or to the recovery of the subject.

If comparing the alteration in the amount measured in step a) with the adequate control of said biomarker, the alteration in the amount of said biomarker in the sample tested corresponds to an increase, the subject of step a) may experience a worsening of the tumor.

If comparing the alteration in the amount measured in step a) with the adequate control of said biomarker, the alteration in the amount of said biomarker in the sample tested corresponds to a decrease, the subject of step a) may experience an improvement of the tumor, or recovery.

In a preferred embodiment, the method further comprises the detection and/or quantification of at least one additional tumor biomarker, and the comparison with an appropriate control sample. Preferably, said additional marker is a pro-inflammatory cytokine effector of the biomarker as defined above, more preferably said pro-inflammatory cytokine is IL-1α, IL-1β, IL-18 or HMGB1.

IL-1α is preferably characterized by the SEQ ID No. 8 or 7.

IL-1β is preferably characterized by the SEQ ID No. 10 or 9.

IL-18 is preferably characterized by the SEQ ID No. 14 or 13.

HMGB1 is preferably characterized by the SEQ ID No. 12 or 11.

Variants, homologues, derivatives or functional fragments of said cytokines and proteins encoded by orthologous genes of said cytokines genes, are included in the definition of the cytokines mentioned above.

In the method according to the present invention, the tumor is preferably lung cancer, more preferably lung carcinoma.

The sample isolated from a subject is preferably a biological fluid, a cell sample and/or a tissue sample.

A further embodiment of the invention is a kit for the diagnosis and/or prognosis and/or for monitoring of the progression of a tumor comprising:
  means for detecting and/or measuring the amount and/or the measuring the alteration in the amount of at least one biomarker as defined above, and optionally
  control means.

Control means may be used to compare the increase in the amount of the biomarker with a value of the appropriate control. The control value can be obtained, for example, with reference to known standards, both from a normal subject, or from normal population.

The means to detect and/or measure the amount and/or measure the alteration in the amount of at least one biomarker as defined above are preferably at least one antibody, an analogue or a functional derivative thereof. Said antibody, analogue or functional derivative thereof may be specific for said biomarker.

The kits according to the invention may further comprise the usual auxiliary components, such as buffers, carriers, dyes, etc. and/or instructions for use.

In the kit according to the present invention, the tumor is preferably lung cancer, more preferably lung carcinoma.

Another embodiment of the invention is a specific inhibitor of the biomarker as defined above, for use in the prevention and/or treatment of the tumor, wherein said inhibitor is preferably an antibody, a vaccine, a siRNA, or a low molecular weight drug.

Said tumor is preferably lung cancer, more preferably lung carcinoma.

A further embodiment of the present invention is an in vitro or ex vivo method for the diagnosis and/or prognosis and/or for monitoring of the development of a tumor characterized by the determination of the presence of a biomarker selected from:
  a) the active form of the human caspase protein;
  b) a variant, a functional derivative or a functional fragment thereof in a biological sample.

According to a preferred embodiment in the method of the present invention, the human caspase protein is the human caspase-4 (SEQ ID No. 1) or the human caspase-1 (SEQ ID No. 2) protein.

In a further preferred embodiment, the method of the present invention comprises the steps of:
  a) determine and/or quantify said biomarker in a sample isolated from a subject, and
  b) compare it with a given control.

A further embodiment of the present invention is the determination and/or quantification of at least one additional tumor marker, and the comparison with an appropriate control sample.

In a preferred embodiment of the present invention, the additional marker is a cytokine effector of the pro-inflammatory cytokine of the biomarker described above, preferably said pro-inflammatory cytokine is IL-1α, IL-1β, IL-18 or HMGB1.

A further embodiment of the present invention is a method characterized in that it determines the increase and/or the decrease of the presence of said biomarker in a biological sample during the prognosis and/or the monitoring of the development and/or progression of a tumor.

According to the present invention, the sample isolated from a subject is a biological fluid, a cell sample and/or a tissue sample.

A further embodiment of the present invention is a kit for the diagnosis and/or prognosis and/or for monitoring of the development and/or progression of a tumor comprising:
  means for determining and/or for measuring the amount and/or for measuring the alteration in the amount of at least one biomarker, and optionally
  a control means.

A further object of the present invention is a specific inhibitor for biomarkers for use in the prevention and/or in the treatment of a tumor, wherein said inhibitor is preferably an antibody, a synthetic peptide, an amino acid and/or nucleotide sequence, a vaccine, a siRNA, or a low molecular weight drug.

According to a preferred embodiment, said inhibitor is an antibody selected from: anti-caspase-1 antibody, anti-caspase-4 antibody, anti-IL-1α antibody, anti-IL-1β antibody, anti-IL-18 antibody, or anti-HMGB1 antibody, or a fragment thereof.

According to a preferred embodiment, said inhibitor is a synthetic peptide inhibitor of the human caspase-1 selected from: Ac-Tyr-Val-Ala-Asp-CHO (y-VAD-CHO) and Ac-Tyr-Val-Ala-Asp-CMK (Ac-Y-VAD-cmk).

According to a preferred embodiment, said inhibitor is an amino acid sequence capable of interfering with the active portion of caspase-4 having the following peptide sequence: GILEGICGTV HDEKKPDVLL YDTIFQIFNN RNCLSLKDKP KVIIVQACRG (SEQ ID No. 15);

According to a preferred embodiment, said inhibitor is a vaccine and/or an antibody obtained after immunization of laboratory animals using the following peptide antigens:

1.
SPNKKAHPNMEAGPC;                         (SEQ ID No. 16)

2.
KKKYYDAKTEDKVRC;                         (SEQ ID No. 17)

3.
CASSQSSENLEEDAV;                         (SEQ ID N: 18)

4.
MAEGNHRKKPLKVLC;                         (SEQ ID N: 19)

5.
CQSFETPRAKAQMPT;                         (SEQ ID N: 20)

6.
PESGESTDALKLCPC;                         (SEQ ID N: 21)

7.
CTEFDHLPPRNGADF;                         (SEQ ID N: 22)

8.
CGLDYSVDVEENLTA;                         (SEQ ID N: 23)

9.
CGTVHDEKKPDVLL;                          (SEQ ID N: 24)

10.
CGANRGELWVRDSPA;                         (SEQ ID N: 25)

11.
CSALRAFATRPEHKS;                         (SEQ ID N: 26)

12.
CIYPIKERNNRTRLA;                         (SEQ ID N: 27)

13.
CIFNNRNCLSLKDKP.                         (SEQ ID N: 28)

According to a preferred embodiment, said inhibitor is a siRNA selected from nucleotide sequences capable of interfering with the mRNA sequence of caspase-4 SEQ ID N. 29 (NCBI reference sequence: NM_01225.3).

In the present invention, the "adequate control" or "appropriate control sample" may be the amount quantified, measured, or evaluated in a sample isolated from a healthy subject or from a patient suffering from another tumor.

In the case of a method for monitoring the progression of a tumor, the amount of adequate control, or of appropriate control sample, could be the amount quantified, measured, or evaluated in a sample isolated from the same subject at various time points before the therapy starts, at various time points during the therapy, etc.

In the in vitro or ex vivo methods according to the present invention, the phase a) is preferably carried out by immunohistochemistry, cytology, ELISA, flow cytometry, or spectrofluorimetry.

In the present invention, the term "detection" refers to any use of any method of observation, detection, or quantification of the signals indicative of the presence of the protein in a sample, or the absolute or relative amount of said target protein in a sample. The methods can be combined with protein or nucleic acid staining methods to provide a signal, for example, via an immunohistochemical staining, ELISA, cell suspension, cytology, fluorescence, radioactivity, colorimetry, gravimetry, X-ray diffraction or adsorption, magnetism, enzyme activities, and similar methods.

In the present invention, the term "quantify" may be understood as a measure of the quantity or concentration or level of the respective protein, preferably semi-quantitative or quantitative. The measurement of a biomarker may be direct or indirect. As used in the specification, the term "amount" refers, but is not limited, to the absolute or relative amount of proteins, and any other value or parameter associated with the same, or that may result from these. Said values or parameters comprise intensity values of the signal obtained by both physical and chemical properties of the protein, obtained by direct measurement, for example, intensity values in an immunoassay, mass spectroscopy, or nuclear magnetic resonance.

Moreover, these values or parameters include those obtained by indirect measurement.

The term "variant" refers to a protein substantially homologous to the biomarker protein as defined above. Generally, a variant includes additions, deletions or substitutions of amino acids. The term "variant" further includes various isoforms of the protein and proteins resulting from post-translational modifications, such as, for example, glycosylation, phosphorylation, or methylation.

The term "derivative or functional fragment" refers to a protein or protein fragment characterized by the same functions of the biomarker as described above, for example having the ability to bind AIM2 and/or induce the release of alarmins such as IL-1α and HMGB1.

When referring to an antibody, the term "fragment" includes scFv (diabody, triabody and tetrabody) fragments, Fab fragments, and F(ab')2 fragments.

The present invention further relates to a method for the prevention of cancer, comprising the identification or detection of a biomarker as defined above. Once the presence of this biomarker is identified, the patient can be subjected to a therapy.

The biomarker as described in the present invention can be used to prevent cancer.

The present invention will be described in non-limiting examples, with reference to the following figures.

FIGURES

FIG. 1. Experimental protocol of lung cancer induction in mice.

Figure 2D:
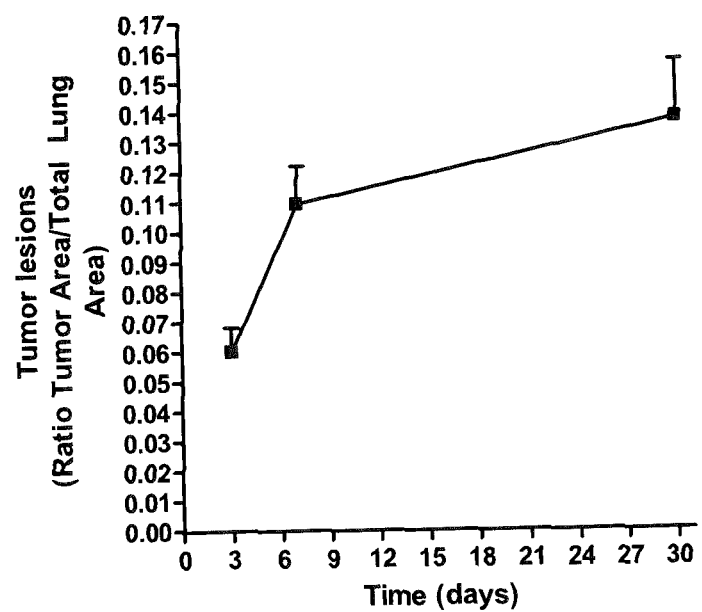

FIG. 2. Analysis of lung cryosections through hematoxylin & eosin staining (H&E) (FIG. 2A), Ki-67 (FIG. 2B), and K-Ras (FIG. 2C). These lung sections were obtained from mice with lung cancer treated with the carcinogen NMU. (FIG. 2D) Quantification of tumor growth (expressed as tumor area/total area) in the lung of mice treated with NMU. Data are expressed as mean±SEM.

Figure 3:
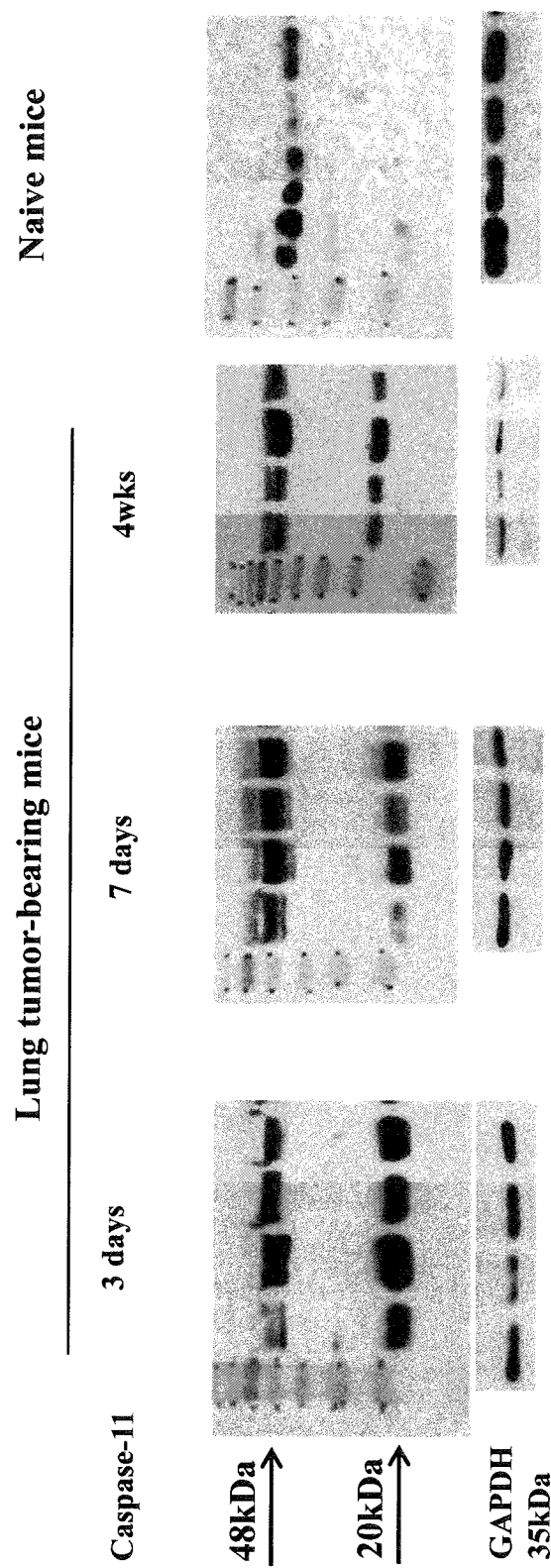

FIG. 3. The active form of caspase-11 (p20 kDa) is present at different time points in the lung of mice with cancer, compared to naïve (untreated) mice that show only the inactive form (p46 kDa).

FIG. 4. A. Tumor growth in C57Bl/6 mice vs. 129Sv mice (A); B. lung cancer growth in C57Bl/6 mice treated with an antibody (Ab) neutralizing the activity of IL-1α, compared to control mice (CTR).

FIG. 5. Activation of caspase-1 (p20 kDa) in C57Bl/6 lung tumor-bearing mice (FIG. 5B), but not in naive (FIG. 5A) and 129Sv (FIG. 5C) mice.

FIG. 6. Reduced tumor lesion in mice genetically deficient in caspase-1 and caspase-11 (caspase-1/11 ko) (*$p<0,0005$, **$p<0,0001$) compared to C57Bl/6 animals (FIG. 6A), data comparable to that obtained in 129Sv animals (FIG. 6B). The pharmacological inhibition with a caspase-1 known specific inhibitor (Ac-Y-VAD-cmk, Sigma Aldrich, cat. N. SML-0429, Ac-Tyr-Val-Ala-Asp-Chloromethylketone; or y-VAD-CHO, Ac-Tyr-Val-Ala-Asp-CHO, Santa Cruz Technologies, USA, cat. N. sc-3069) reduced the tumor lesion in C57Bl/6 mice exposed to NMU (*$p<0.05$, **$p<0.01$) (FIG. 6C), even if this injury was not comparable to that observed in caspase-1/11 ko and 129Sv mice (FIG. 6D).

Figure 7:
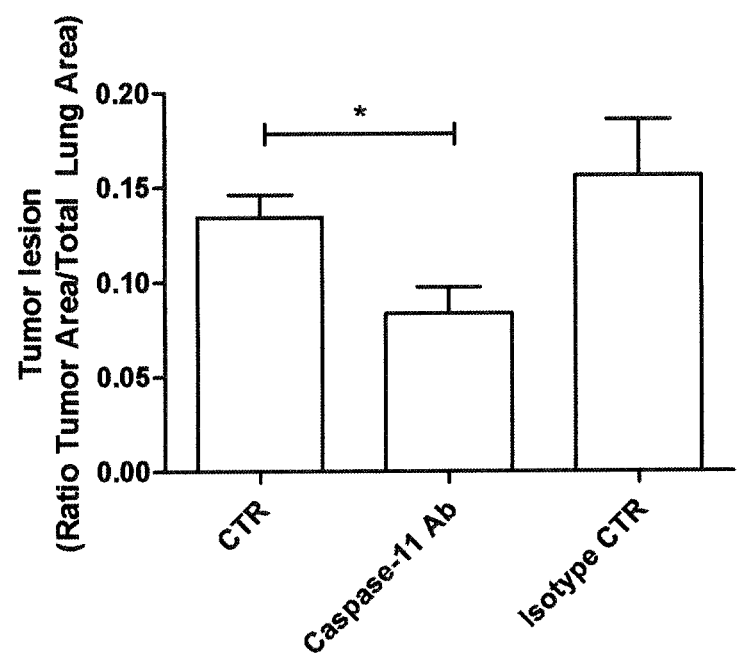

FIG. 7. The administration of an antibody capable of inhibiting the activity of caspase-11 significantly reduced (*$p<0.05$) the tumor mass compared to control animals or animals treated with the control isotype (rabbit IgG).

Figure 8A:
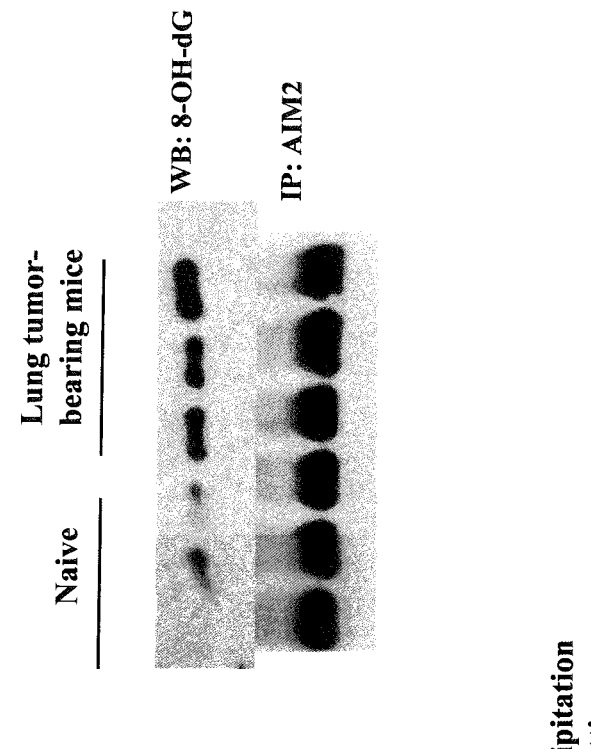
Figure 8B:
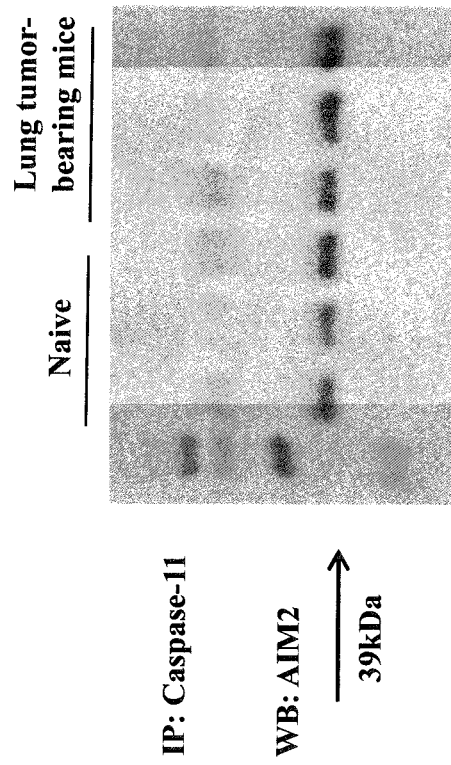

FIG. 8. Immunoprecipitation experiments. FIG. 8A) Caspase-11 binds AIM2 inflammasome complex; FIG. 8B) AIM2 binds to 8-OH-dG.

FIG. 9. A. Presence of the precursor (p48-kDa) and the active form of caspase 4 (p20 kDa) (A) in lung homogenates obtained from patients with lung cancer. The lung 'healthy' portion of the same patient is identified with H, while the neoplastic one is identified with LC.

Figure 9A:
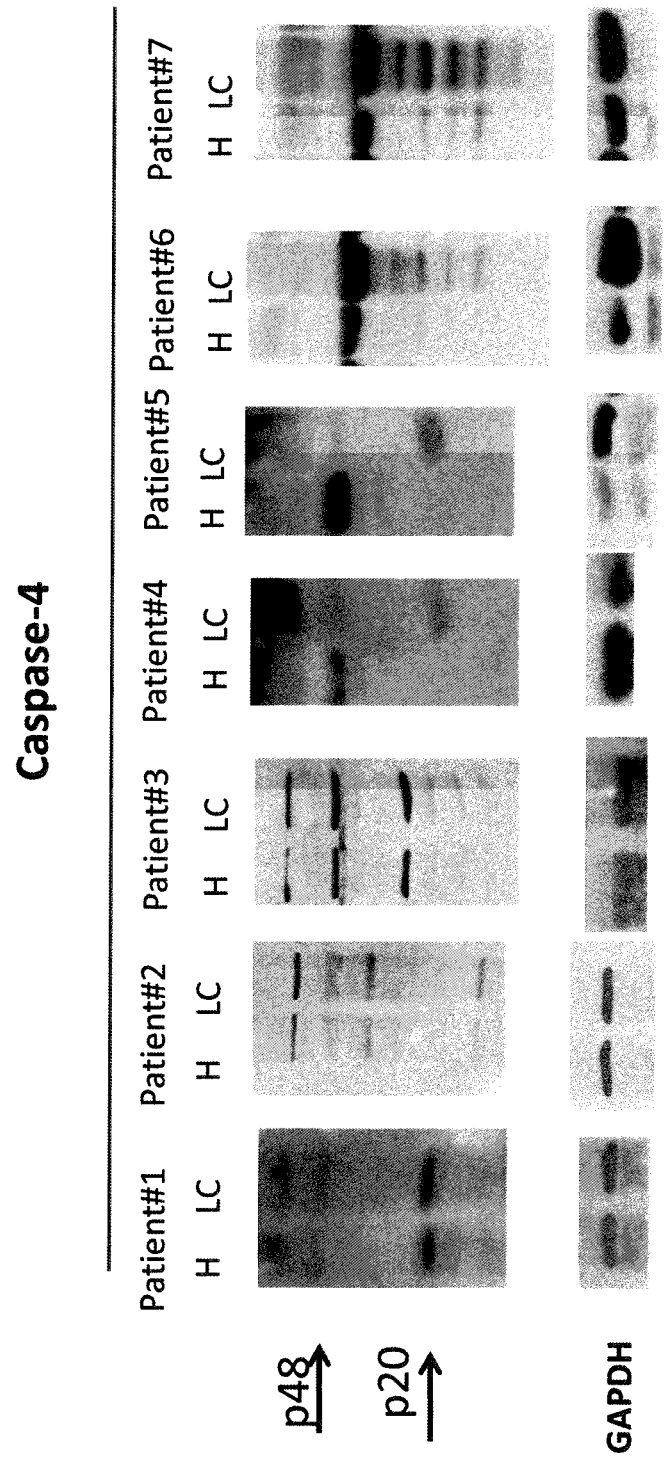
Figure 9B:
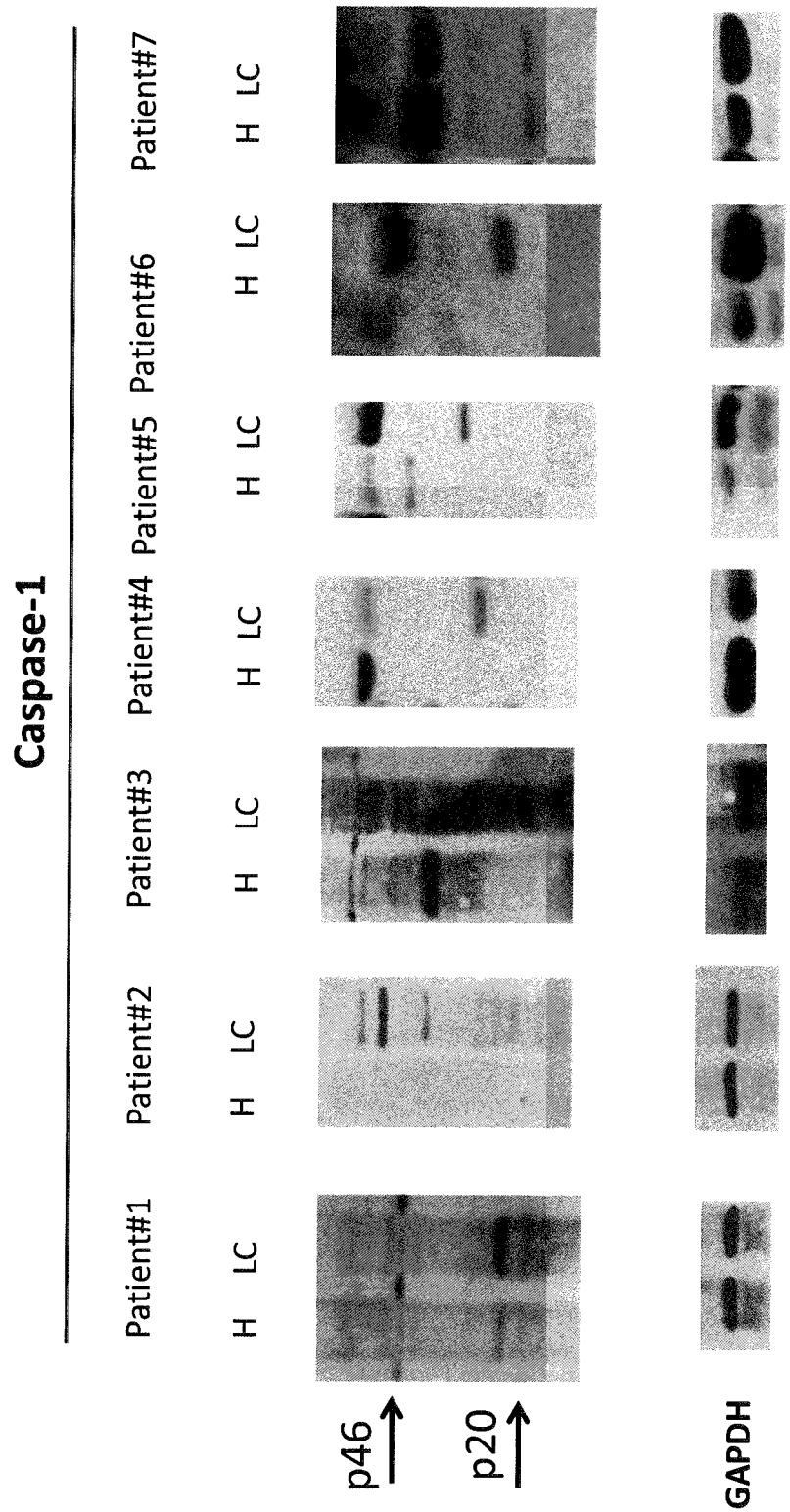

FIG. 9B. Presence of the precursor (p46 kDa) and the active form of caspase-1 (p20 kDa) in lung homogenates of patients with lung cancer.

Figure 10B:
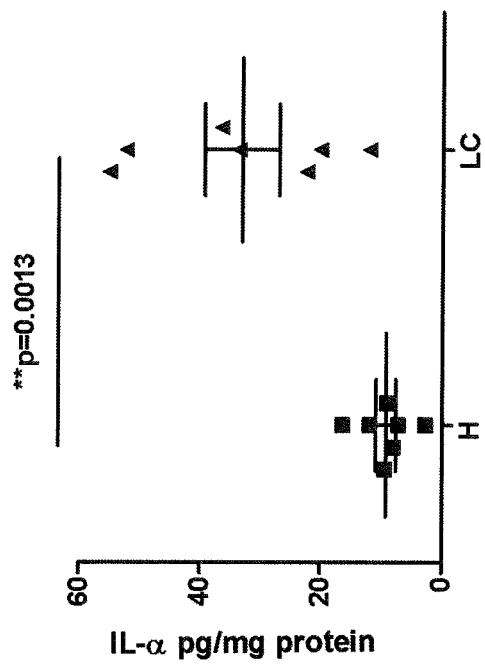
Figure 10A:
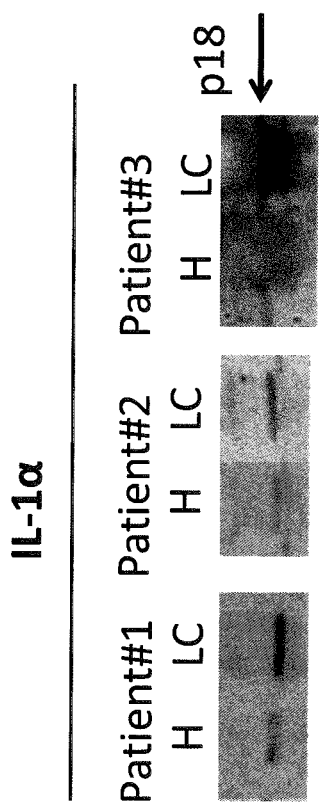
Figure 10C:
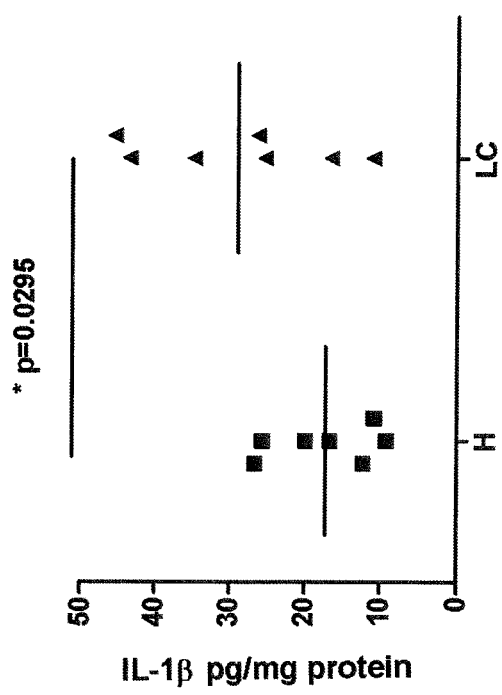

FIG. 10. A. presence of the active portion of IL-1α in patients with cancer (LC) compared to healthy ones (H); FIG. 10 B. quantification by ELISA of IL-1α, expressed as pg/mg of lung tissue analysed, C. levels of IL-1β in homogenates of human lung, healthy and with lung cancer.

Figure 11:
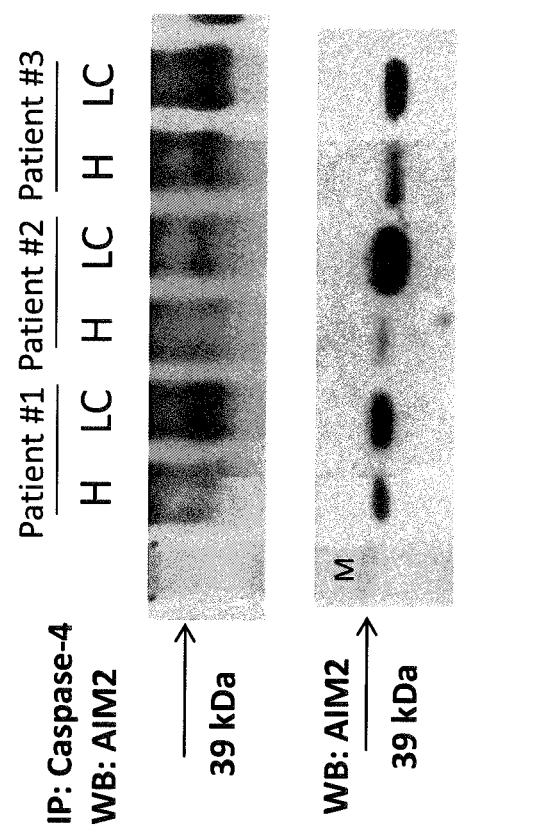

FIG. 11. Immunoprecipitation experiments on lung homogenates, healthy (H) and with neoplastic lesion (LC). Caspase-4 binds the AIM2 inflammasome complex.

Figure 12:
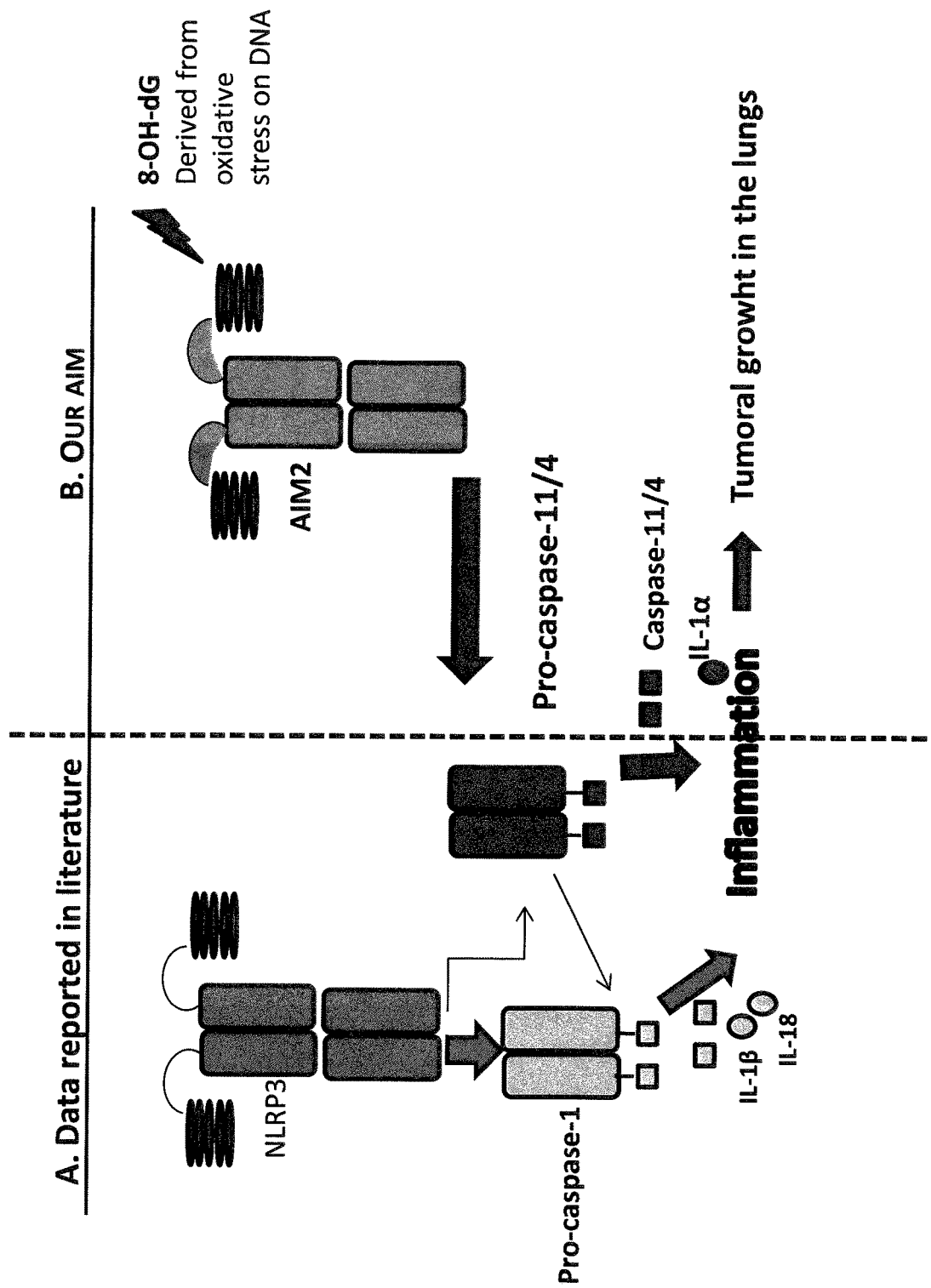

FIG. 12. Flow Chart representing what is reported in the literature (A) compared to what has now be found by these authors (B). A. It is known that, as a result of infection with pathogens, the canonical inflammasome dependent caspase-1 pathway is activated. The release of pro-inflammatory cytokines such as IL-1β and IL-18 [NCBI accession numbers: mouse: NP_032386.1] (SEQ ID No. 13); human: [AAH07461.1 (SEQ ID No. 14)] provides a cascade of events that amplify the pro-inflammatory response, so that the host is able to promote the pathogen clearance. Conversely, in a tumor context, (B) caspase-11 in the mouse and caspase-4 in humans are involved in the induction of an inflammatory response, as a result of the priming of the AIM2-dependent inflammasome complex. This mechanism is activated in response to AIM2 recognition of hydroxylated nucleosides (8-OH-dG), markers of oxidative stress.

EXAMPLES

Materials and Methods

Murine Model of Lung Carcinoma.

C57Bl/6 mice (Harlan Laboratories, Italy) and 129Sv mice, and caspase-1 and 11 knockout mice (Charles River Laboratories, Italy) (females of 6-8 weeks) were subjected to intratracheal (i.t.) instillation of a carcinogen, N-nitroso-N-methyl-urea (NMU), having alkylating and mutagenic activities (Damiani et al., 2008). NMU was administered three times every 7 days, according to the following administration schedule and dosage: day 0, 50 µg/mouse; day 8, 10 µg/mouse and day 15, 10 µg/mouse (FIG. 1). In some experiments, an anti-IL-1α antibody (Ab) (2 µg/rat i.p.; eBioscience, USA), or a caspase-1 inhibitor (Ac-Y-VAD-cmk: 10 ug/mouse i.p., Sigma Aldrich, USA), or an anti-caspase-11 antibody (10 ug/mouse, i.p.; Santa Cruz, USA) were administered to C57Bl/6 mice treated with NMU. The animals were sacrificed at different time points (3-7-30 days from the first NMU administration), according to the scheme shown in FIG. 1. The tumor lesion was expressed as the tumor lesion area/total lung area ratio.

Human Samples of Lung Carcinoma.

The human samples were obtained following thoracic surgery and lung resection in patients with stage III carcinoma of epithelioid origin, adenocarcinoma of the non-small cell lung cancer type. The healthy portion, indicated with H, was obtained from a lung portion macroscopically very far from the cancerous area. The human tissues were provided by the Department of Thoracic Surgery of the Azienda Ospedaliera Universitaria San Giovanni di Dio e Ruggi d'Aragona, Salerno, Italy (informed consent was obtained).

Western Blotting Analysis.

The murine lungs and the human samples were digested with a digestion solution consisting of collagenase (1 U/ml) and DNAse I (20 µg/ml). Following protein determination, the samples were loaded (50 µg/sample) on 12% polyacrylamide gel, then transferred on to a nitrocellulose membrane. Anti-caspase-4 (Santa Cruz, USA), anti-caspase-1 (Santa Cruz, USA), anti-caspase-11 (Santa Cruz, USA), anti-IL-1α (R&D Systems, UK) antibodies were used. The loading control was performed by GAPDH recognition.

In another set of experiments, the human or murine homogenates were immunoprecipitated by using magnetic microbeads (Invitrogen, USA) capable of binding the primary antibody (caspase-11, or caspase-4, or AIM2) and the specific antigen. In a second phase, the co-localization of the target recognized by the primary antibody, with AIM2 or 8-OH-dG, was evaluated by using the appropriate antibodies in order to detect the presence or absence of AIM2 or 8-OH-dG.

ELISA.

Human and murine lung homogenates were tested for the presence of IL-1α and IL-1β, following the instructions provided by the kit manufacturer (eBioscience, USA) (informed consent was obtained).

Immunohistochemistry Analysis.

The left lobes of mice treated with NMU were fixed in OCT medium (TedPella Inc., Milan, Italy), then cut into 7-12 µm cryosections, and stained with hematoxylin & eosin (H&E) to highlight the morphological characteristics of the tissue to be correlated to the cryosections subjected to immunofluorescent staining for identifying K-Ras presence (Cell Signalling, UK) in the lung cancer lesion, and/or to cryosections subjected to immunohistochemical analyses according to the diaminobenzidine method (DAB) in order to detect the immune complexes consisting of Ki-67, tumor marker, (Invitrogen, Italy) with the secondary HRP antibody. The control isotype for Ki-67 (anti-rat IgG) was used as negative control.

Statistical Analysis.

The results are expressed as mean±SEM. The differences between the various groups were statistically analyzed using One Way ANOVA analysis and/or Student's t test, as appropriate. The p-values lower than 0.05 were considered statistically significant.

Results

1. Caspase-11 is Involved in Lung Cancer Growth in the Mouse.

In C57Bl/6 mice, the treatment with NMU produced tumor lesions, as indicated by the lung cryosections (FIG. 2A) that were positive for tumor proliferation markers, such as Ki-67 (FIG. 2B), and K-Ras (FIG. 2C). In mice treated with NMU, the tumor masses growth, calculated as the ratio between the tumor area and the total area, is of exponential type (FIG. 2D).

A very interesting finding, object of the present invention, was the observation that the caspase-11 was active from day 3 after NMU administration up to 4 weeks (FIG. 3) compared to naïve mice (untreated) which did not show the active form of the enzyme (p20 kDa), but only the inactive form (p48 kDa).

Figure 4A:
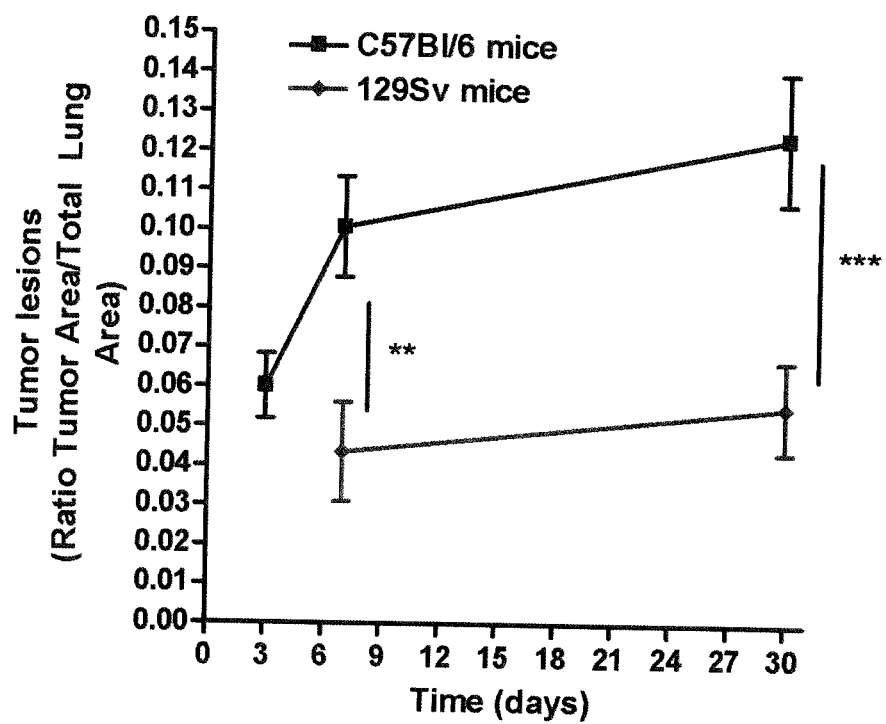
Figure 4B:
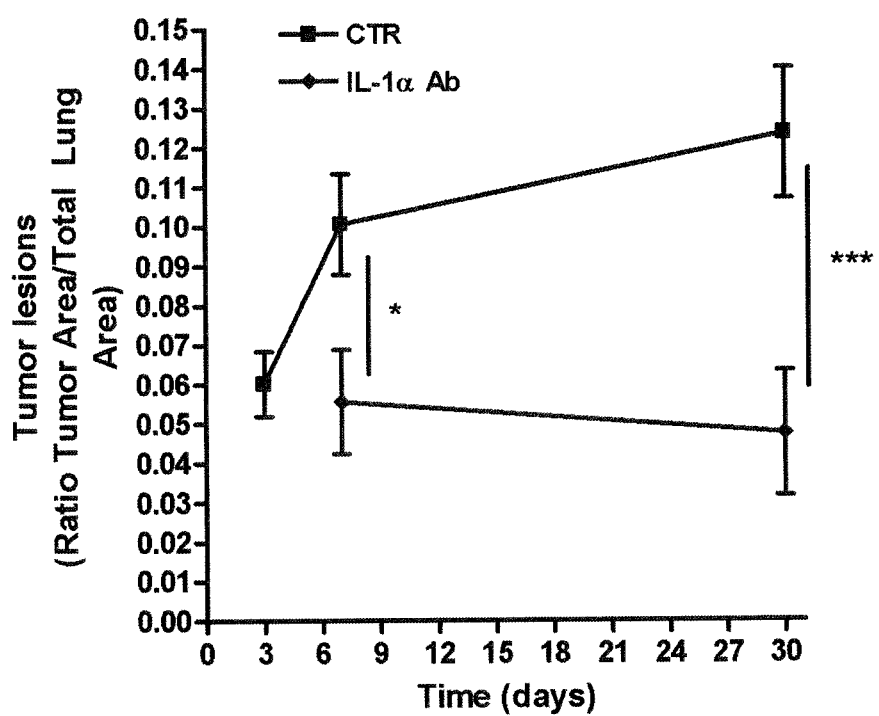

In order to highlight the role of caspase-11 in lung tumor growth, 129Sv mice, deficient in caspase-11 (Kayagaki et al., 2011) were used. 129Sv mice treated with NMU developed an extremely small tumor mass (7 days: 0.043±0.013; 30 days: 0.055±0.012) compared to C57131/6 mice receiving the same treatment (7 days: 0.101±0.013; 30 days: ±0.123 0.016) (FIG. 4A; p<0.01; *p<0.005). Furthermore, being caspase-11 involved in the release of alarmins, such as IL-1α (Ng and Monack, 2013), C57Bl/6 animals treated at the same time with NMU and with an anti-IL-1α antibody, showed a significant reduction of the tumor lesion (7 days: 0.056±0.013, p<0.05; 0.047±0.016, 30 days: p<0.005) (FIG. 4B), fully comparable to tumor development observed in 129Sv mice (7 days: 0.043±0.013; 30 days: 0.055±0.012) deficient in caspase-11. This finding strongly corroborates the role of caspase-11 in lung tumor growth in mice.

Since it has been reported that caspase-11 can induce the activation of the non-canonical inflammasome pathway through caspase-1 activation (Case et al., 2013), we observed that also in our experimental model, the caspase-1 was activated at different time points (3-7-30 days) compared to naïve mice, as shown in FIG. 5B vs. 5A. It was also interestingly observed that caspase-1 was not activated in 129Sv mice treated with NMU (FIG. 5C), implying a close correlation between caspase-1 activity and the presence of functional caspase-11 in lung tumor growth.

Figure 6A:
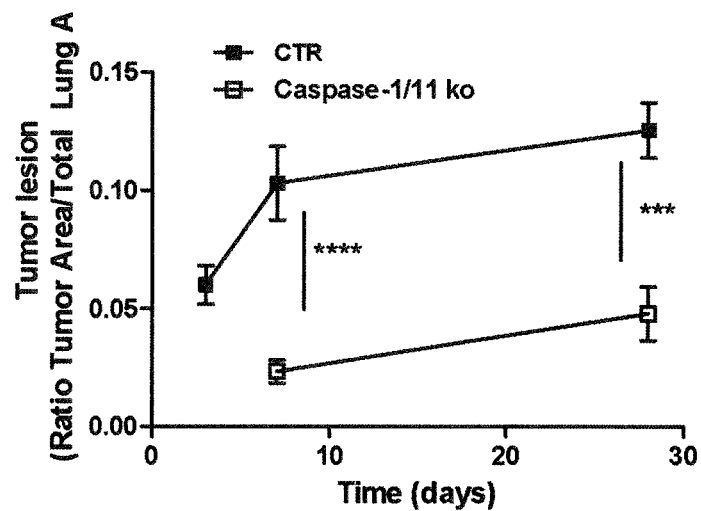
Figure 6B:
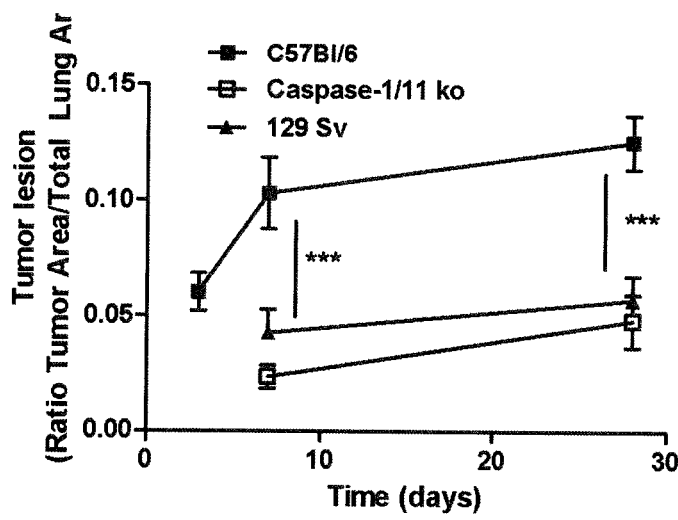
Figure 6C:
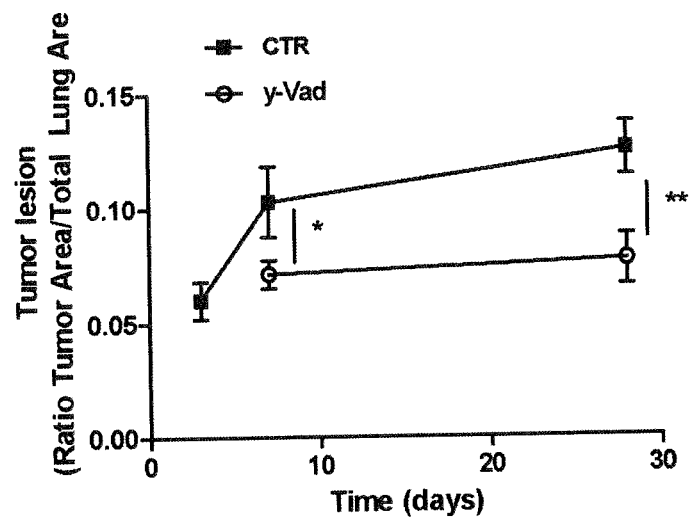
Figure 6D:
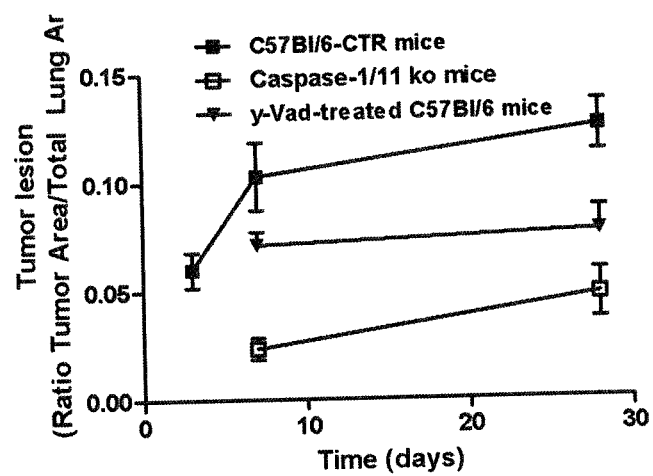

In support to this, mice genetically deficient in caspase-1 and caspase-11 (caspase-1/11 ko) showed a smaller tumor lesion (*p<0.0005, **p<0.0001) compared to C57Bl/6 animals (FIG. 6A). Moreover, these data were comparable to those obtained in 129Sv animals exposed to NMU (FIG. 5C), thus implying that caspase-11 plays a pivotal role for lung carcinogenesis (FIG. 6B). Additionally, in support of the above statements, the C57Bl/6 animals exposed to NMU were treated with a known specific caspase-1 inhibitor (Ac-Y-VAD-cmk: y-VAD). As shown in FIG. 6C, the tumor lesion was reduced (*p<0.05, **p<0.01) in animals treated with y-VAD, although this injury was not comparable to that observed in caspase-1/11 ko and 129Sv mice (FIG. 6D). These data corroborate a main activity of caspase-11, that 'orchestrate' caspase-1 activity during lung carcinogenesis.

Moreover, treatment of mice with an antibody capable of inhibiting caspase-11 activity significantly reduced (*p<0.05) the tumor mass compared to controls or treated animals with the control isotype (rabbit IgG) (FIG. 7).

It is well known in the literature that caspase-11 is able to induce caspase-1 activation through NLRP3, one of the inflammasome components (Case et al., 2013). Since in our experimental model the activation of caspase-11 in C57Bl/6 (FIG. 3) is associated with active caspase-1 (FIG. 5), while in 129Sv mice, lacking of caspase-11, caspase-1 is not active (FIG. 5C), an immunoprecipitation analysis was performed on samples of lung homogenates from mice C57Bl/6, naïve and treated with NMU. This experiment was performed to determine the caspase-11 binding to inflammasome components, such as NLRP3 and AIM2. Western Blotting analyses show that caspase-11 is able to bind AIM2, but not NLRP3 (not revealed in this immunoprecipitation analysis: data not shown) (FIG. 8A). Moreover, it was observed that the activation of AIM2, that binds to caspase-1 (Schroder and Tschopp, 2010) and caspase-11 (as demonstrated herein), was induced by hydroxylated guanosine derivatives (8-OH-dG) (FIG. 8). Specifically, 8-OH-dG detection by Western Blotting on AIM2 immunoprecipitates of lung homogenates obtained from naïve or NMU-treated C57Bl/6 mice showed that 8-OH-dGs were bound to AIM2 in mice with lung tumor, compared to naïve mice (FIG. 8B). This finding has never been reported in the literature, and provides a new mechanism of action for caspase-11 involvement in the non-canonical inflammasome pathway during lung carcinogenesis in mice.

2. Caspase-4 is Active in Human Tumor Tissues of Lung Carcinoma.

In order to make the present study translational, the role of the human analogue of caspase-11, i.e. caspase-4, was analyzed. The caspase-4 was active (p20 kDa) in all the tumor tissues analysed from 7 patients, as compared to healthy tissues (FIG. 9A). Moreover, in the same tissues, the caspase-1 was found to be activated (p20 kDa) more in the tumor portion than in the healthy one (FIG. 9B). Therefore, the presence of the activity of these enzymes in humans is similar to that observed in mice. In addition, IL-1α (FIGS. 10A and B, **p<0.005) and IL-1β (FIG. 10B, *p<0.05) presence was higher in the tumor tissues than in normal tissue. Similarly to what observed in the mouse, caspase 4 was associated with AIM2, as demonstrated by immunoprecipitation experiments followed by Western Blotting analyses performed on homogenate tissues of human healthy lung and lung with tumor lesions (FIG. 11).

These data show for the first time that the active forms of the caspase proteins, particularly caspase-4 (in humans) and caspase-1, and of the proteins encoded by orthologous genes of the respective human caspases genes, in particular by the orthologue gene of the human caspase-4 gene, preferably caspase-11 (in the mouse), are involved in lung tumorigenesis.

Compared to what is reported in the literature in the mouse (panel A of FIG. 12), the present authors have shown that, in addition to the role of caspase-11/4 in the tumor growth, the latter is in turn activated by AIM2 bound to 8-OH-DG, guanosine hydroxylated derivatives, which are a result of the oxidative stress underlying the inflammasome activation, which in turn may promote neoplastic growth induced by carcinogens (panel B of FIG. 12).

BIBLIOGRAPHY

Allen, I. C., TeKippe, E. M., Woodford, R.-M. T., Uronis, J. M., Roll, E. K., Rogers, A. B., Herfarth, H. H., Jobin, C., and Ting, J. P.-Y. (2010). The NLRP3 inflammasome functions as a negative regulator of tumorigenesis during colitis-associated cancer. J. Exp. Med. 207, 1045-1056.

Bortoluci, K. R., and Medzhitov, R. (2010). Control of infection by pyroptosis and autophagy: role of TLR and NLR. Cell. Mol. Life Sci. CMLS 67, 1643-1651.

Caffrey, D. R., and Fitzgerald, K. A. (2012). Select Inflammasome Assembly. Science 336, 420-421.

Case, C. L., Kohler, L. J., Lima, J. B., Strowig, T., de Zoete, M. R., Flavell, R. A., Zamboni, D. S., and Roy, C. R. (2013). Caspase-11 stimulates rapid flagellin-independent pyroptosis in response to Legionella pneumophila. Proc. Natl. Acad. Sci. U.S.A. 110, 1851-1856.

Chow, M. T., Sceneay, J., Paget, C., Wong, C. S. F., Duret, H., Tschopp, J., Möller, A., and Smyth, M. J. (2012a). NLRP3 suppresses NK cell-mediated responses to carcinogen-induced tumors and metastases. Cancer Res. 72, 5721-5732.

Chow, M. T., Tschopp, J., Möller, A., and Smyth, M. J. (2012b). NLRP3 promotes inflammation-induced skin cancer but is dispensable for asbestos-induced mesothelioma. Immunol. Cell Biol. 90, 983-986.

Coussens, L. M., Zitvogel, L., and Palucka, A. K. (2013). Neutralizing tumor-promoting chronic inflammation: a magic bullet? Science 339, 286-291.

Damiani, L. A., Yingling, C. M., Leng, S., Roma, P. E., Nakamura, J., and Belinsky, S. A. (2008). Carcinogen-induced gene promoter hypermethylation is mediated by DNMT1 and causal for transformation of immortalised bronchial epithelial cells. Cancer Res. 68, 9005-9014.

Dostert, C., Pétrilli, V., Van Bruggen, R., Steele, C., Mossman, B. T., and Tschopp, J. (2008). Innate immune activation through Nalp3 inflammasome sensing of asbestos and silica. Science 320, 674-677.

Ghiringhelli, F., Apetoh, L., Tesniere, A., Aymeric, L., Ma, Y., Ortiz, C., Vermaelen, K., 25 Panaretakis, T., Mignot, G., Ullrich, E., et al. (2009). Activation of the NLRP3 inflammasome in dendritic cells induces IL-1beta-dependent adaptive immunity against tumors. Nat. Med. 15, 1170-1178.

Jett, J. R., Cortese, D. A., and Fontana, R. S. (1983). Lung cancer: Current concepts and prospects. CA. Cancer J. Clin. 33, 74-86. 30

Kayagaki, N., Warming, S., Lamkanfi, M., Vande Walle, L., Louie, S., Dong, J., Newton, K., Qu, Y., Liu, J., Heldens, S., et al. (2011). Non-canonical inflammasome activation targets caspase-11. Nature 479, 117-121.

Kayagaki, N., Wong, M. T., Stowe, I. B., Ramani, S. R., Gonzalez, L. C., Akashi-Takamura, S., Miyake, K., Zhang, J., Lee, W. P., Muszyński, A., et al. (2013). Noncanonical inflammasome activation by intracellular LPS independent of TLR4. Science 341, 1246-1249.

Lamkanfi, M., and Dixit, V. M. (2012). Inflammasomes and their roles in health and disease. Annu. Rev. Cell Dev. Biol. 28, 137-161.

Latz, E., Xiao, T. S., and Stutz, A. (2013). Activation and regulation of the inflammasomes. Nat. Rev. Immunol. 13, 397-411.

Ng, T. M., and Monack, D. M. (2013). Revisiting caspase-11 function in host defense. Cell Host Microbe 14, 9-14. 10

Paul-Clark, M. J., George, P. M., Gatheral, T., Parzych, K., Wright, W. R., Crawford, D., Bailey, L. K., Reed, D. M., and Mitchell, J. A. (2012). Pharmacology and therapeutic potential of pattern recognition receptors. Pharmacol. Ther. 135, 200-215.

Pinto, A., Morello, S., and Sorrentino, R. (2011). Lung cancer and Toll-like receptors. Cancer Immunol. Immunother. CII 60, 1211-1220.

Schroder, K., and Tschopp, J. (2010). The inflammasomes. Cell 140, 821-832.

Valavanidis, A., Fiotakis, K., and Vlachogianni, T. (2008). Airborne particulate matter and human health: toxicological assessment and importance of size and composition of particles for oxidative damage and carcinogenic mechanisms. J. Environ. Sci. Health Part C Environ. Carcinog. Ecotoxicol. Rev. 26, 339-362. 20

Zitvogel, L., Kepp, O., Galluzzi, L., and Kroemer, G. (2012). Inflammasomes in carcinogenesis and anticancer immune responses. Nat. Immunol. 13, 343-351.

Yamauchi M. Yamaguchi R. et al., PLOS One, Vol. 7 (9), e43923-e43923 (2012).

The invention claimed is:

1. A method of treating a tumor in a subject, said method comprising:
    (a) determining the level of the active form of human caspase-4 (SEQ ID NO:1) in a sample isolated from the subject;
    (b) selecting the subject with an increased level of activated form of human caspase-4 when compared to a normal control; and
    (c) administering a specific inhibitor of an active form of human caspase-4 protein (SEQ. ID NO:1), and said inhibitor is a synthetic peptide selected from the group consisting of Ac-Tyr-Val-Ala-Asp-CHO (y-VAD-CHO) and Ac-Tyr-Val-Ala-Asp-CMK (Ac-Y-VAD-cmk), and wherein the tumor is a lung cancer.

2. The method according to claim 1, wherein the lung cancer is a lung carcinoma.

3. The method according to claim 1, further comprising determining the level of at least one additional tumor marker.

4. The method of claim 3, wherein the additional marker is a proinflammatory cytokine effector.

5. The method of claim 1, wherein the sample is a biological fluid, a cell sample or a tissue sample.

6. The method according to claim 1, wherein the human caspase-4 protein has an active portion having the amino acid sequence GILEGICGTV HDEKKPDVLL YDTIF-QIFNN RNCLSLKDKP KVIIVQACRG (SEQ ID NO: 15).

* * * * *